US010695043B2

(12) United States Patent
Scheller et al.

(10) Patent No.: US 10,695,043 B2
(45) Date of Patent: Jun. 30, 2020

(54) SURGICAL INSTRUMENT SUBCOMPONENT INTEGRATION BY ADDITIVE MANUFACTURING

(71) Applicant: Katalyst Surgical, LLC, Chesterfield, MO (US)

(72) Inventors: Gregg D Scheller, Wildwood, MO (US); Eric J Bass, Webster Groves, MO (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 122 days.

(21) Appl. No.: 15/882,430

(22) Filed: Jan. 29, 2018

(65) Prior Publication Data

US 2018/0235594 A1  Aug. 23, 2018

Related U.S. Application Data

(60) Provisional application No. 62/461,573, filed on Feb. 21, 2017.

(51) Int. Cl.
*A61B 17/02* (2006.01)
*A61F 9/008* (2006.01)
(Continued)

(52) U.S. Cl.
CPC ...... *A61B 17/0231* (2013.01); *A61B 17/2909* (2013.01); *A61B 17/30* (2013.01);
(Continued)

(58) Field of Classification Search
CPC .............................. A61B 17/0231; B33Y 80/00
See application file for complete search history.

(56) References Cited

U.S. PATENT DOCUMENTS

| 1,371,288 A | 3/1921 | Wolhaupter |
| 1,736,731 A | 11/1929 | Breeding |

(Continued)

FOREIGN PATENT DOCUMENTS

| WO | WO1997015234 A1 | 5/1997 |
| WO | WO1998037819 A1 | 9/1998 |

(Continued)

OTHER PUBLICATIONS

Steve Charles, Techniques and tools for dissection of epiretinal membranes, Graefe' Arch Clin Exp Ophthalmol, 241:347-352, 2003.

(Continued)

*Primary Examiner* — Christian A Sevilla

(57) ABSTRACT

Surgical instrument subcomponent integration by additive manufacturing may include identifying at least two subcomponents of a multi-component assembly wherein a first subcomponent of the at least two subcomponents has a first functionality and wherein the first subcomponent of the at least two subcomponents is manufactured from a first material having a first set of material properties. Surgical instrument subcomponent integration by additive manufacturing may include modifying one or more properties of the first subcomponent of the at least two subcomponents to reproduce the first functionality when the first subcomponent is manufactured from a second material having a second set of material properties. Surgical instrument subcomponent integration by additive manufacturing may comprise integrating the at least two subcomponents by manufacturing an integral component by additive manufacturing wherein the integral component is manufactured from the second material and wherein the first functionality is retained.

15 Claims, 19 Drawing Sheets

(51) Int. Cl.
*B33Y 80/00* (2015.01)
*A61F 9/007* (2006.01)
*A61B 17/30* (2006.01)
*A61B 17/29* (2006.01)
*A61B 17/00* (2006.01)

(52) U.S. Cl.
CPC .............. *A61F 9/007* (2013.01); *A61F 9/008* (2013.01); *B33Y 80/00* (2014.12); *A61B 2017/003* (2013.01); *A61B 2017/00526* (2013.01); *A61B 2017/2918* (2013.01); *A61B 2017/305* (2013.01); *A61F 9/00736* (2013.01)

(56) References Cited

U.S. PATENT DOCUMENTS

| | | | |
|---|---|---|---|
| 2,549,731 A | 4/1951 | Wattley | |
| 3,659,607 A * | 5/1972 | Banko | A61B 17/32002 |
| | | | 606/169 |
| 4,135,868 A | 1/1979 | Schainholz | |
| 4,504,264 A | 3/1985 | Kelman | |
| 4,541,992 A | 9/1985 | Jerge et al. | |
| 4,553,957 A | 11/1985 | Williams et al. | |
| 4,610,252 A | 9/1986 | Catalano | |
| 4,626,248 A * | 12/1986 | Scheller | A61F 9/00736 |
| | | | 600/575 |
| 4,706,666 A | 11/1987 | Sheets | |
| 4,739,761 A | 4/1988 | Grandon | |
| 4,798,292 A | 1/1989 | Hauze | |
| 4,959,199 A | 9/1990 | Brewer | |
| 5,190,050 A | 3/1993 | Nitzsche | |
| 5,215,726 A | 6/1993 | Kudla et al. | |
| 5,222,973 A | 6/1993 | Sharpe et al. | |
| 5,227,313 A | 7/1993 | Gluck et al. | |
| 5,286,255 A | 2/1994 | Webber | |
| 5,318,589 A | 6/1994 | Lichtman | |
| 5,346,677 A | 9/1994 | Risk | |
| 5,355,871 A | 10/1994 | Hurley et al. | |
| 5,370,658 A | 12/1994 | Scheller et al. | |
| 5,384,103 A | 1/1995 | Miller | |
| 5,415,645 A | 5/1995 | Friend et al. | |
| 5,425,730 A | 6/1995 | Luloh | |
| 5,433,190 A * | 7/1995 | Sunalp | A61B 17/0231 |
| | | | 600/236 |
| 5,433,929 A | 7/1995 | Riihimaki et al. | |
| 5,451,230 A | 9/1995 | Steinert | |
| 5,527,313 A | 6/1996 | Scott et al. | |
| 5,601,581 A | 2/1997 | Fogarty et al. | |
| 5,636,639 A | 6/1997 | Turturro et al. | |
| 5,647,115 A | 7/1997 | Slater et al. | |
| 5,695,514 A | 12/1997 | Chin | |
| D393,067 S | 3/1998 | Geary et al. | |
| D393,715 S | 4/1998 | Strickland | |
| 5,759,502 A | 6/1998 | Spencer et al. | |
| 5,792,165 A | 8/1998 | Klieman et al. | |
| 5,810,811 A | 9/1998 | Yates et al. | |
| 5,843,387 A | 12/1998 | Dane et al. | |
| 5,851,197 A | 12/1998 | Marano et al. | |
| 5,893,873 A | 4/1999 | Rader et al. | |
| 5,893,877 A | 4/1999 | Gampp, Jr. et al. | |
| 5,913,422 A | 6/1999 | Cote et al. | |
| 5,916,159 A | 6/1999 | Ryan, Jr. | |
| 5,921,998 A | 7/1999 | Tano et al. | |
| 6,099,550 A | 8/2000 | Yoon | |
| 6,159,162 A | 12/2000 | Kostylev et al. | |
| 6,183,467 B1 | 2/2001 | Shapeton et al. | |
| 6,183,480 B1 * | 2/2001 | Mackool | A61B 17/0231 |
| | | | 606/107 |
| 6,277,100 B1 | 8/2001 | Raulerson et al. | |
| D453,222 S | 1/2002 | Garito et al. | |
| 6,419,675 B1 | 7/2002 | Gallo, Sr. | |
| D463,555 S | 9/2002 | Etter et al. | |
| 6,451,037 B1 | 9/2002 | Chandrasekaran et al. | |
| 6,488,695 B1 | 12/2002 | Hickingbotham | |
| 6,551,129 B2 | 4/2003 | Kato | |
| 6,572,565 B2 | 6/2003 | Daley et al. | |
| 6,575,989 B1 | 6/2003 | Scheller et al. | |
| 6,616,683 B1 | 9/2003 | Toth et al. | |
| 6,675,805 B1 * | 1/2004 | Graether | A61B 17/0231 |
| | | | 128/849 |
| 6,730,076 B2 | 5/2004 | Hickingbotham | |
| 6,749,601 B2 | 6/2004 | Chin | |
| 6,772,765 B2 | 8/2004 | Scheller et al. | |
| 6,800,076 B2 | 10/2004 | Humayun | |
| 6,863,668 B2 | 3/2005 | Gillespie et al. | |
| 6,908,476 B2 | 6/2005 | Jud et al. | |
| 6,926,728 B2 | 8/2005 | Zucherman et al. | |
| 6,945,984 B2 | 9/2005 | Arumi et al. | |
| 7,077,848 B1 * | 7/2006 | de Juan, Jr. | A61F 9/007 |
| | | | 606/108 |
| 7,338,494 B2 | 3/2008 | Ryan | |
| D565,733 S | 4/2008 | Andre | |
| 7,438,717 B2 | 10/2008 | Tylke | |
| 7,632,242 B2 | 12/2009 | Griffin et al. | |
| 7,731,728 B2 | 6/2010 | Glaser | |
| 7,766,904 B2 | 8/2010 | Mc Gowan, Sr. et al. | |
| 7,783,346 B2 | 8/2010 | Smith et al. | |
| D625,412 S | 10/2010 | Garito et al. | |
| 7,935,080 B2 | 5/2011 | Howell et al. | |
| 8,038,692 B2 | 10/2011 | Valencia et al. | |
| 8,197,468 B2 | 6/2012 | Scheller et al. | |
| 8,202,288 B2 | 6/2012 | Ryan | |
| 8,425,473 B2 * | 4/2013 | Ho | A61F 9/007 |
| | | | 604/264 |
| 8,821,444 B2 | 9/2014 | Scheller et al. | |
| 9,138,346 B2 | 9/2015 | Scheller et al. | |
| 9,149,389 B2 | 10/2015 | Scheller et al. | |
| 9,204,995 B2 | 12/2015 | Scheller et al. | |
| 9,226,762 B2 | 1/2016 | Scheller et al. | |
| 9,427,251 B2 | 8/2016 | Rethy et al. | |
| 10,413,445 B2 * | 9/2019 | Scheller | A61F 9/00736 |
| 2001/0056286 A1 | 12/2001 | Etter et al. | |
| 2002/0115902 A1 | 8/2002 | Dejuan, Jr. et al. | |
| 2003/0171762 A1 | 9/2003 | Forchette et al. | |
| 2003/0229976 A1 | 12/2003 | Scheller et al. | |
| 2005/0154403 A1 | 7/2005 | Sauer et al. | |
| 2005/0245950 A1 | 11/2005 | Kozlowski | |
| 2006/0036270 A1 | 2/2006 | Terao | |
| 2006/0235382 A1 | 10/2006 | Cohen et al. | |
| 2007/0104609 A1 | 5/2007 | Powell | |
| 2007/0106246 A1 | 5/2007 | Modesitt | |
| 2007/0185514 A1 | 8/2007 | Kirchhevel | |
| 2007/0282348 A1 | 12/2007 | Lumpkin | |
| 2008/0183199 A1 | 7/2008 | Attinger | |
| 2008/0195135 A1 | 8/2008 | Attinger | |
| 2008/0255526 A1 | 10/2008 | Bosse et al. | |
| 2009/0030427 A1 | 1/2009 | Razvi et al. | |
| 2009/0112258 A1 | 4/2009 | Kreidler | |
| 2009/0131870 A1 | 5/2009 | Fiser | |
| 2009/0228066 A1 | 10/2009 | Hirata et al. | |
| 2009/0318856 A1 | 12/2009 | Glaser | |
| 2010/0023050 A1 | 1/2010 | Reinauer et al. | |
| 2010/0063359 A1 | 3/2010 | Okoniewski | |
| 2010/0145381 A1 | 6/2010 | Moon | |
| 2010/0228226 A1 | 9/2010 | Nielsen | |
| 2011/0015669 A1 | 1/2011 | Corcosteugi | |
| 2012/0116361 A1 | 5/2012 | Hanlon et al. | |
| 2012/0150216 A1 | 6/2012 | Hickingbotham et al. | |
| 2012/0179172 A1 | 7/2012 | Paul, Jr. et al. | |
| 2012/0191120 A1 | 7/2012 | Linsi | |
| 2013/0071507 A1 | 3/2013 | Scheller et al. | |
| 2013/0085326 A1 | 4/2013 | Scheller et al. | |
| 2013/0197488 A1 | 8/2013 | Scheller et al. | |
| 2014/0012314 A1 | 1/2014 | Dai et al. | |
| 2014/0066977 A1 | 3/2014 | Scheller et al. | |
| 2014/0121697 A1 | 5/2014 | Scheller et al. | |
| 2014/0128909 A1 | 5/2014 | Scheller et al. | |
| 2014/0135820 A1 | 5/2014 | Schaller | |
| 2014/0142603 A1 | 5/2014 | Scheller et al. | |
| 2014/0163363 A1 | 6/2014 | Scheller et al. | |
| 2014/0172010 A1 | 6/2014 | Vezzu | |
| 2014/0277110 A1 | 9/2014 | Scheller et al. | |
| 2015/0088193 A1 | 3/2015 | Scheller et al. | |
| 2015/0173944 A1 | 6/2015 | Linsi et al. | |

(56) References Cited

U.S. PATENT DOCUMENTS

| | | |
|---|---|---|
| 2017/0079675 A1 | 3/2017 | Scheller et al. |
| 2017/0086871 A1 | 3/2017 | Scheller et al. |
| 2017/0100114 A1 | 4/2017 | Scheller et al. |
| 2017/0340380 A1 | 11/2017 | Scheller et al. |
| 2017/0361034 A1 | 12/2017 | Scheller et al. |
| 2018/0014849 A1 | 1/2018 | Scheller et al. |

FOREIGN PATENT DOCUMENTS

| | | |
|---|---|---|
| WO | WO2002041796 A2 | 5/2002 |
| WO | WO2014140808 A1 | 9/2014 |
| WO | WO2015026957 A1 | 2/2015 |
| WO | WO2017066026 A1 | 4/2017 |
| WO | WO2017218161 A1 | 12/2017 |
| WO | WO2018017296 A1 | 1/2018 |

OTHER PUBLICATIONS http://www.bpf.co.uk/plastipedia/polymers/polyamides.aspx [Mar. 20, 2017 4:57:01 PM].

Cummins, Kate, The rise of additive manufacturing, (May 24, 2010); https://www.theengineer.co.uk/issues/24-may-2010/the-rise-of-additive-manufacturing/.

* cited by examiner

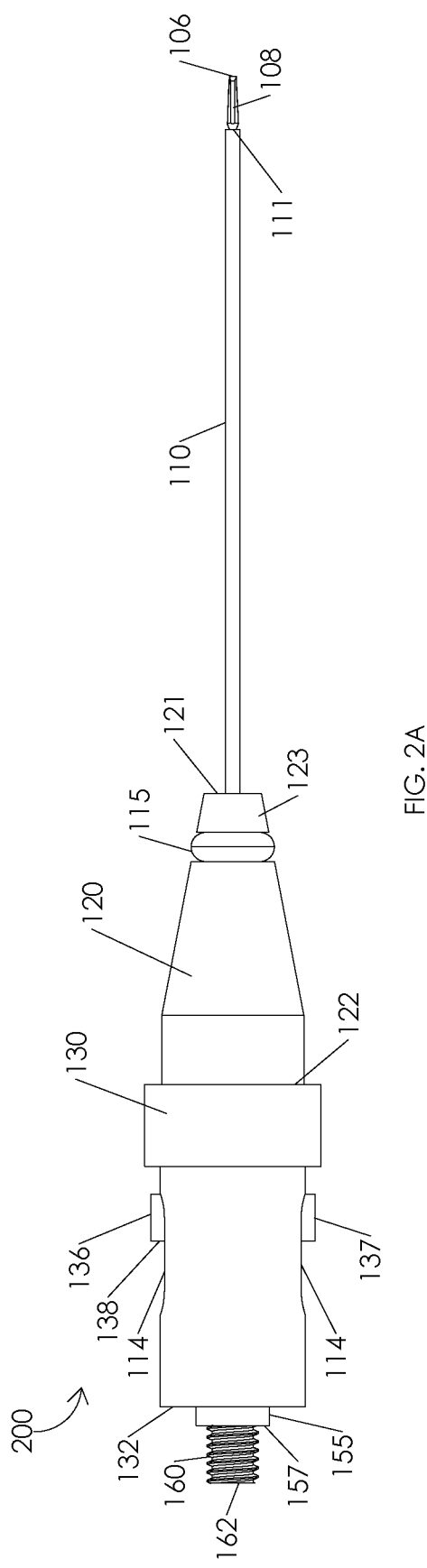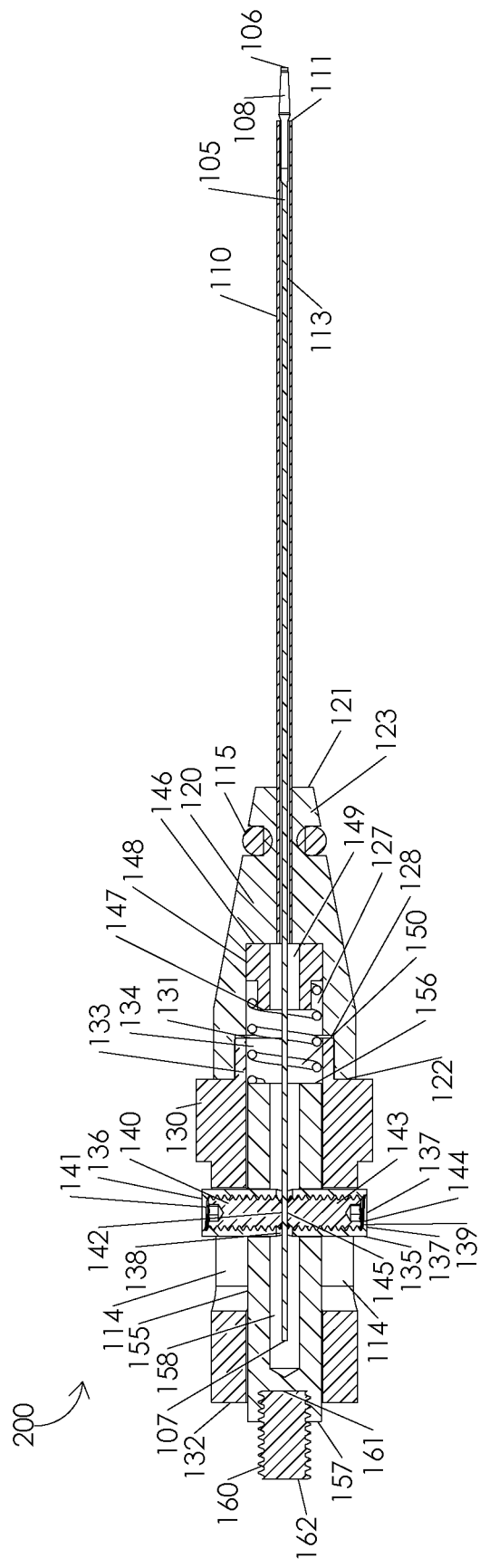
FIG. 2A
FIG. 2B

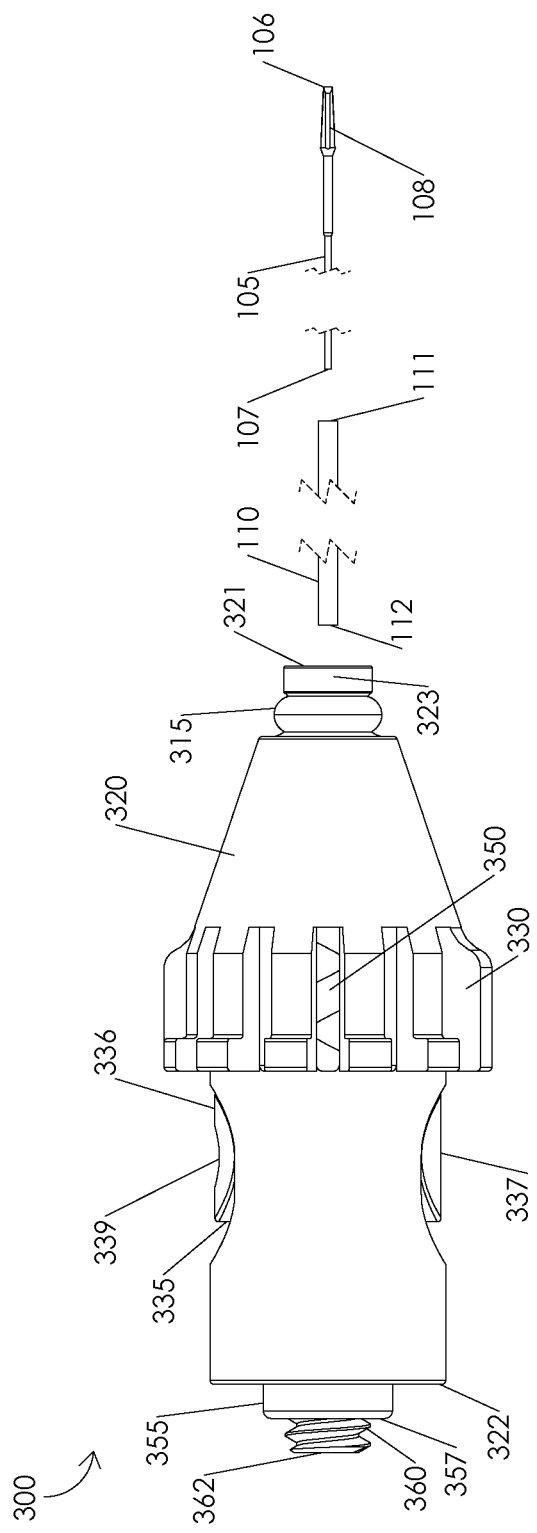
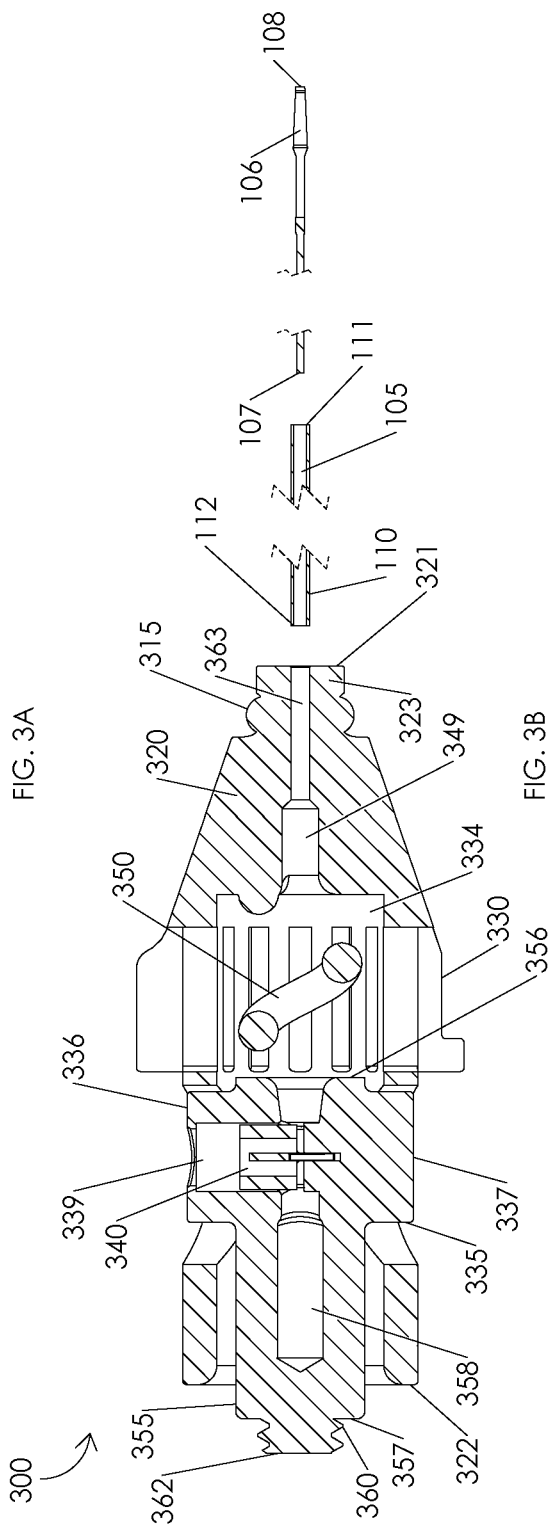
FIG. 3A
FIG. 3B

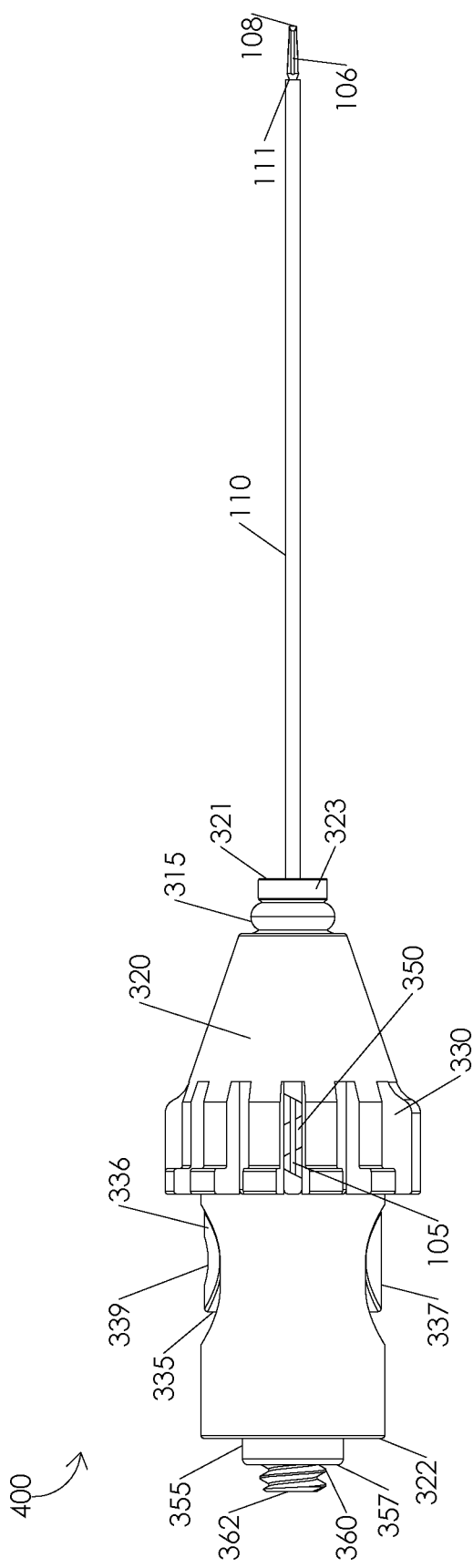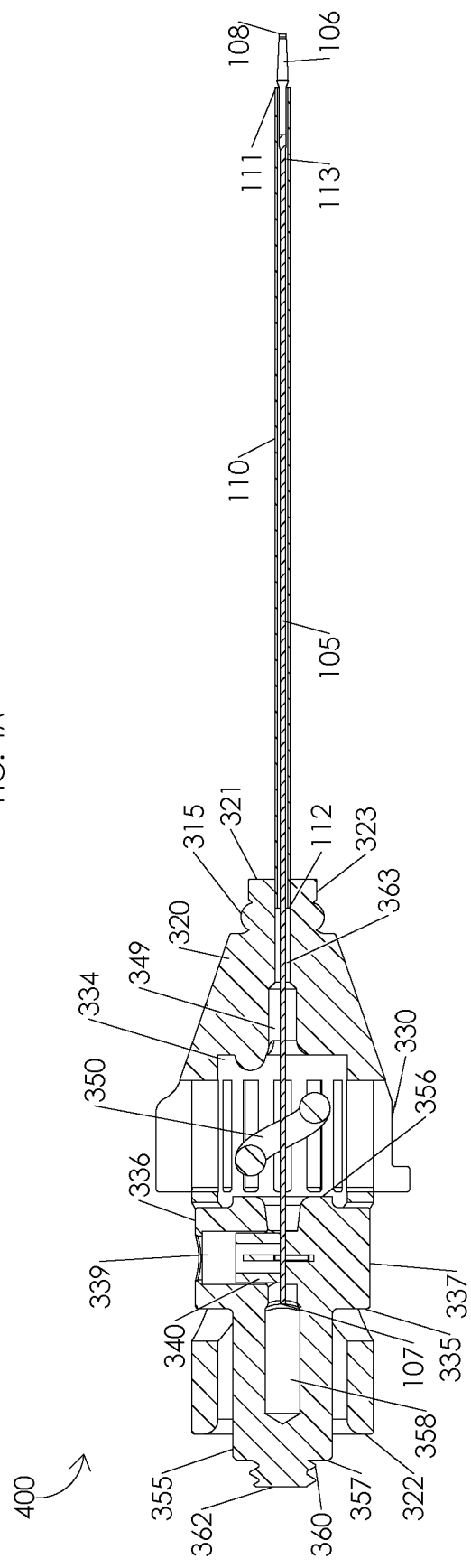
FIG. 4A
FIG. 4B

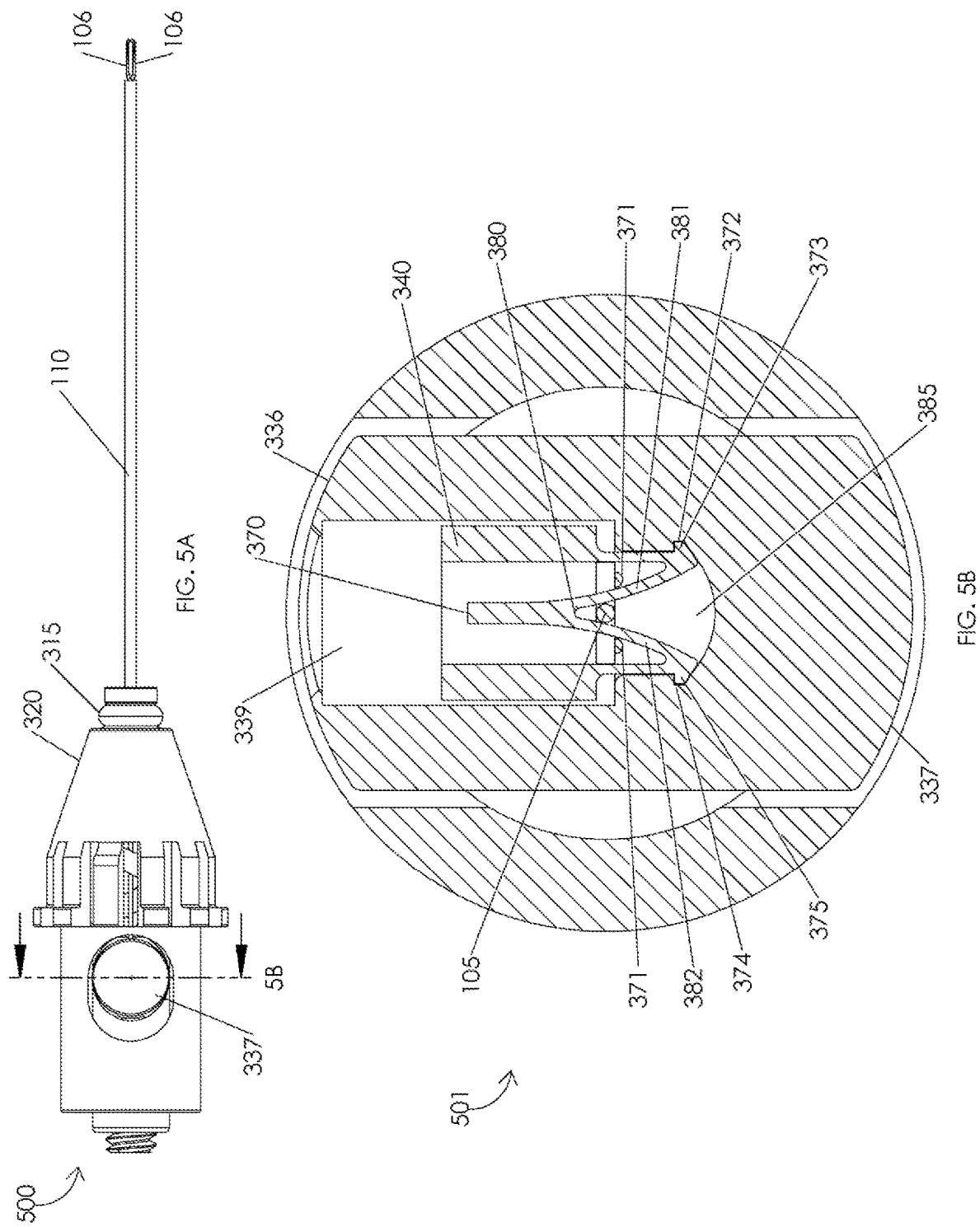

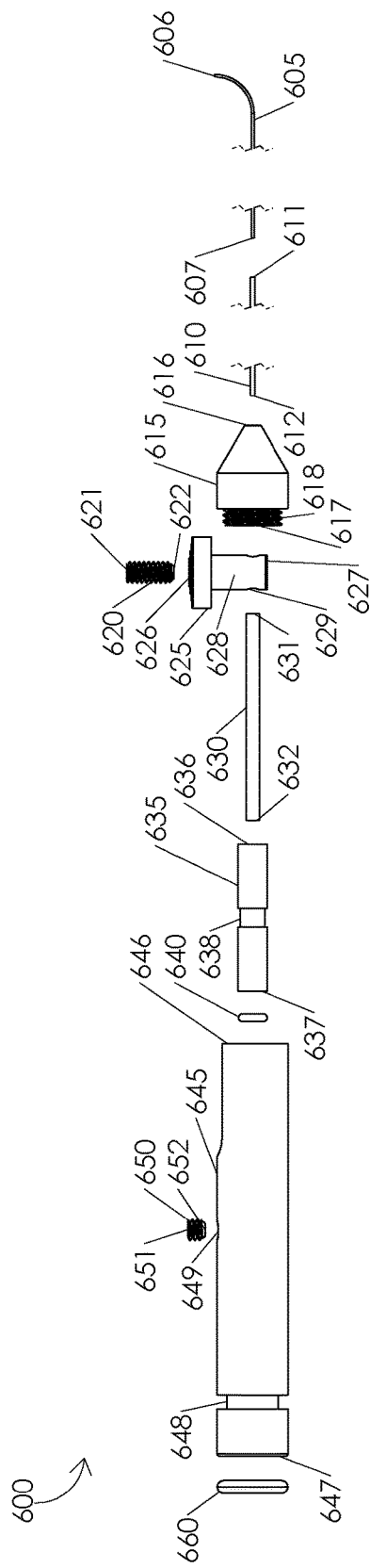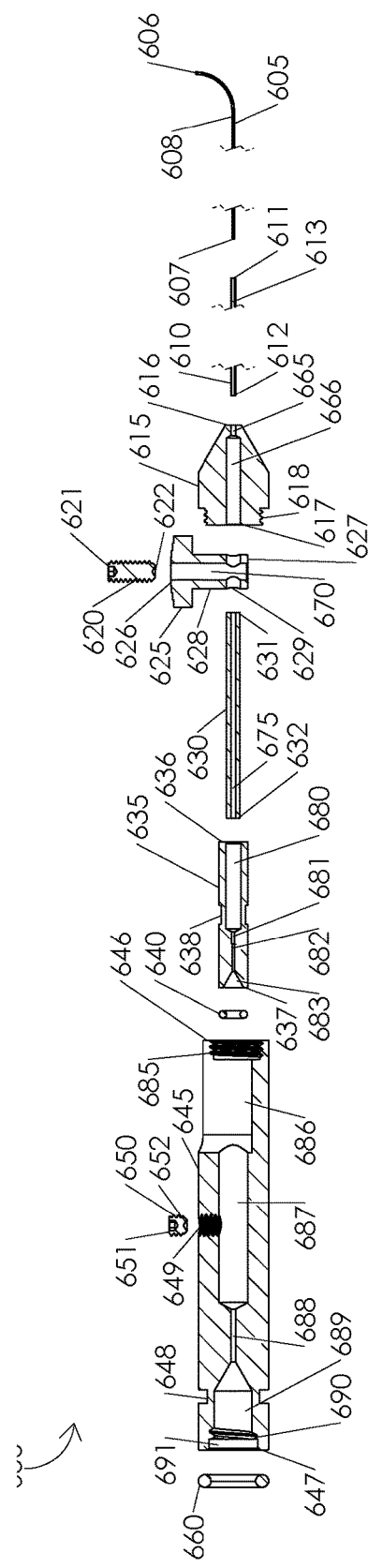
FIG. 6A
FIG. 6B

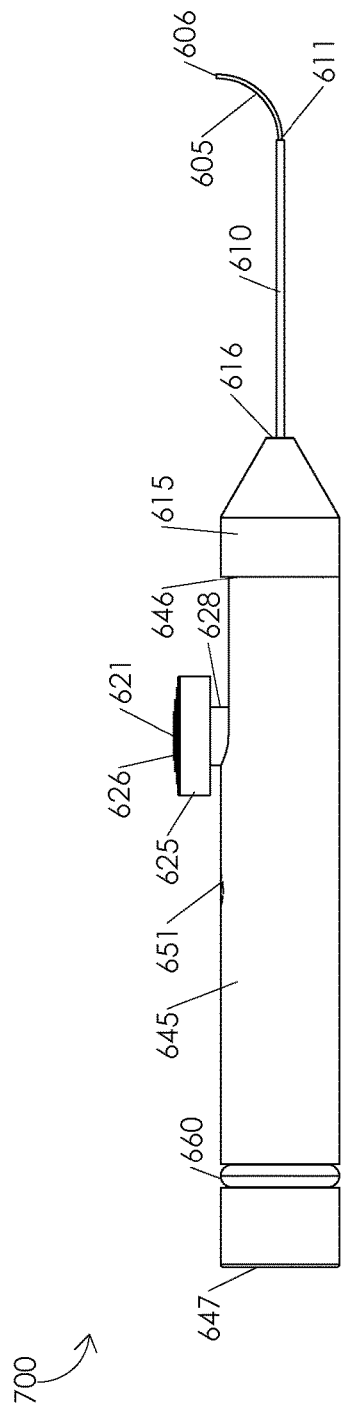
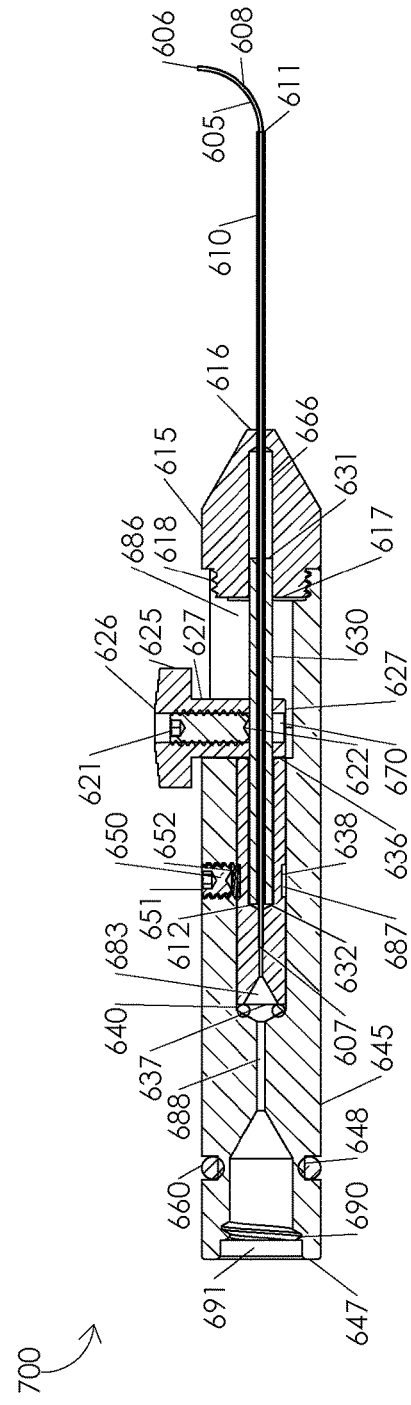
FIG. 7A
FIG. 7B

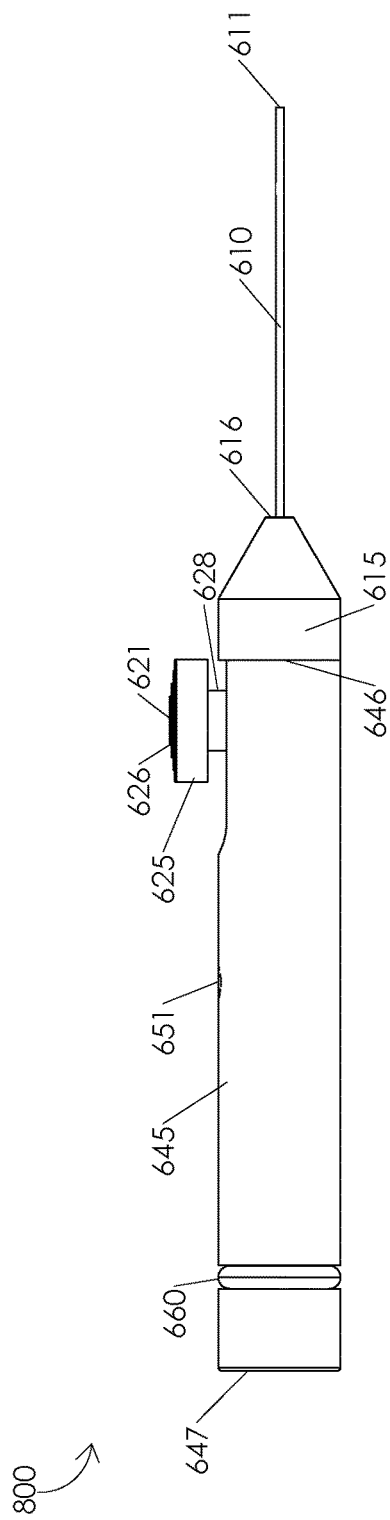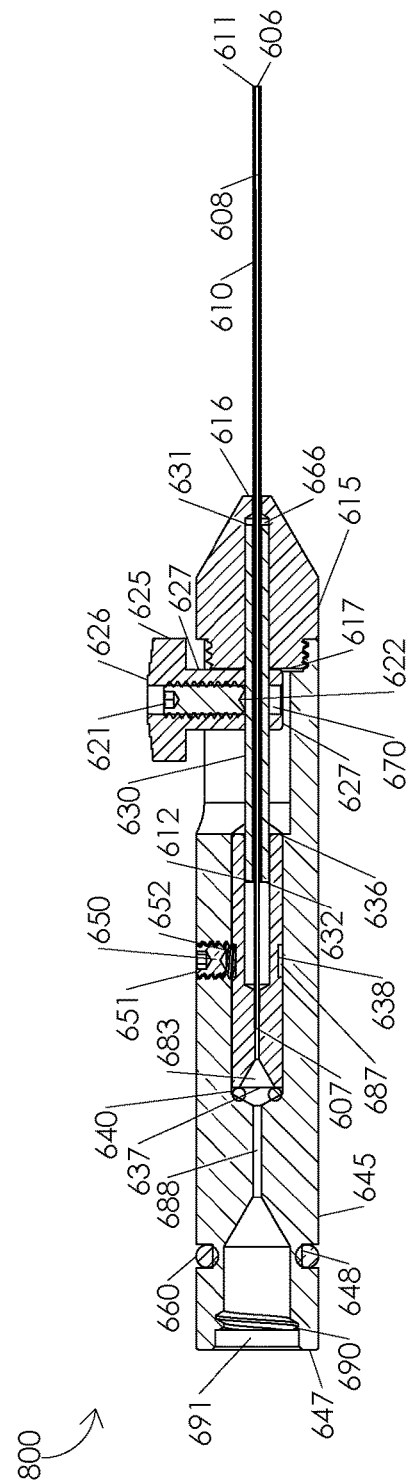

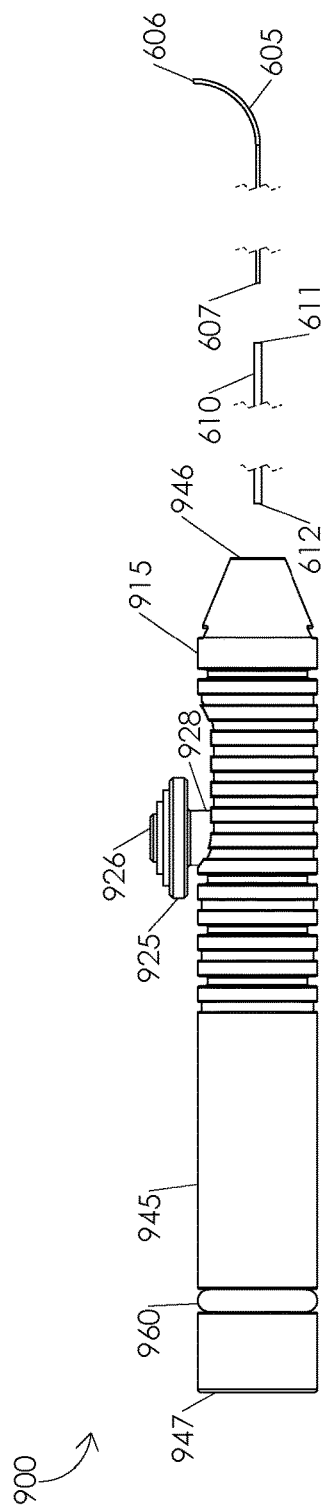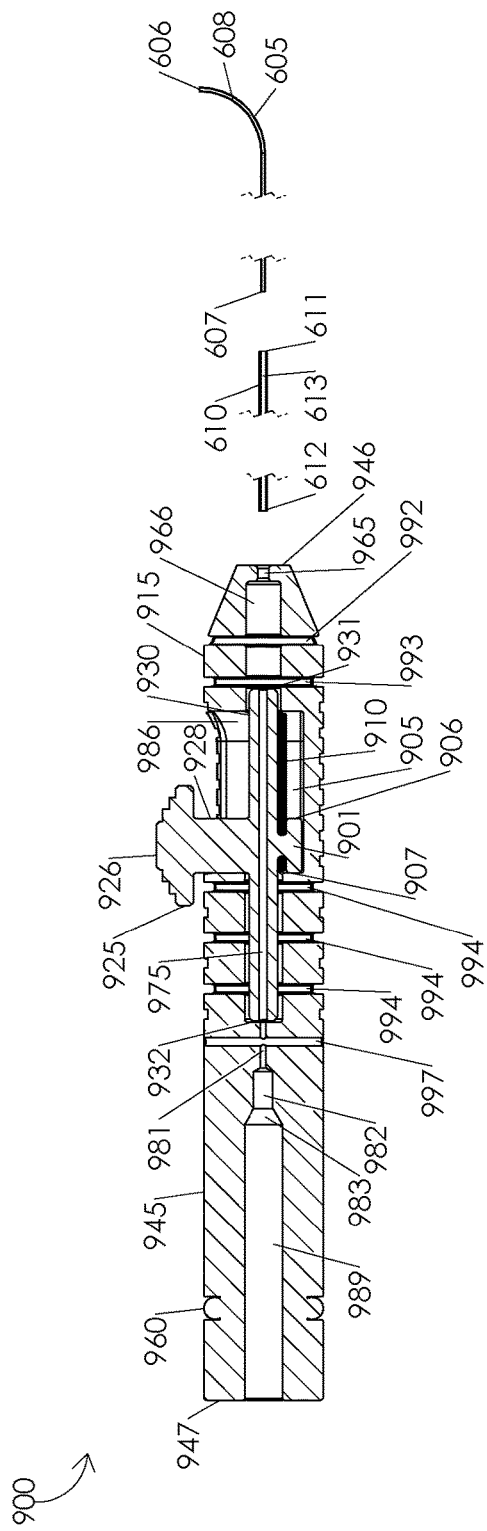

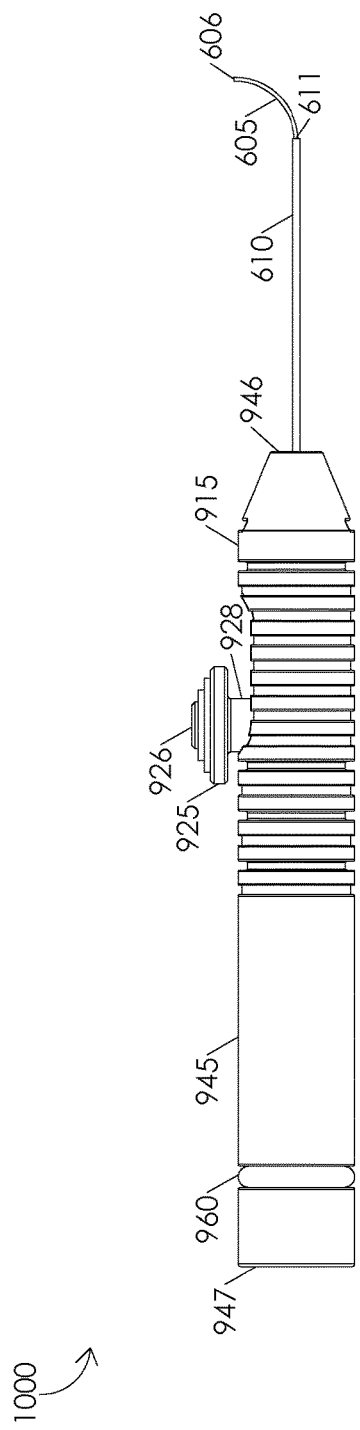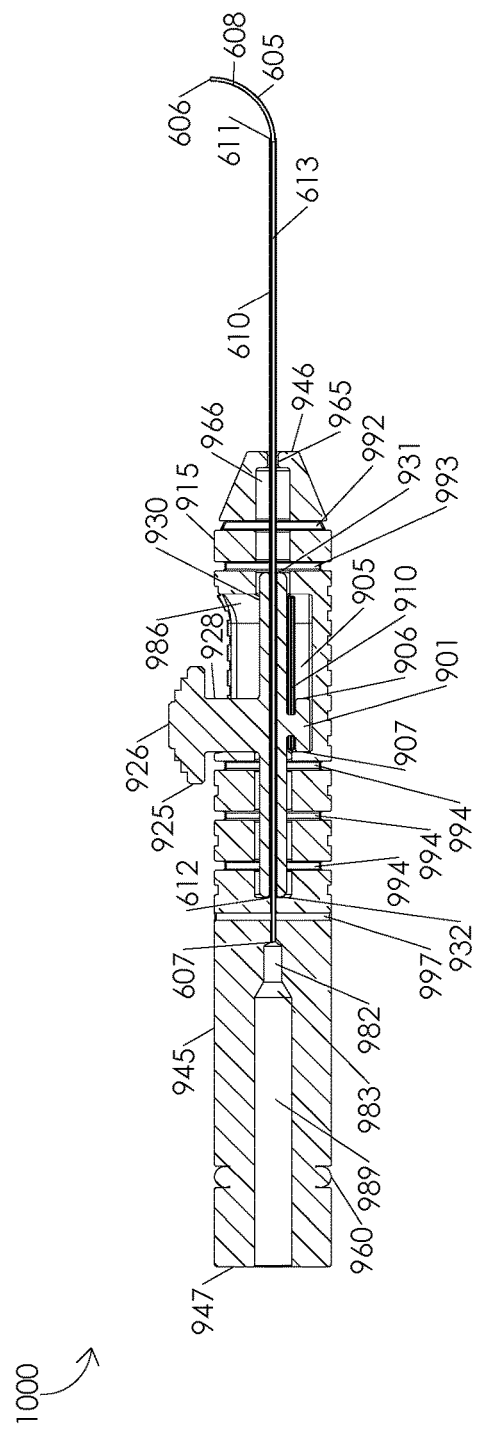
FIG. 10A
FIG. 10B

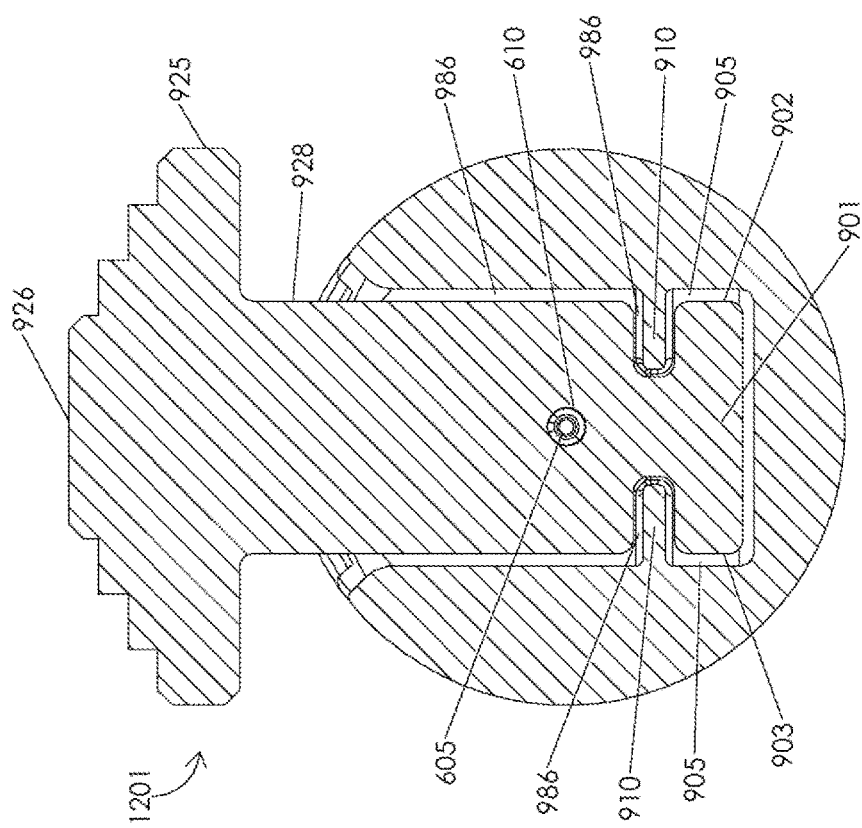
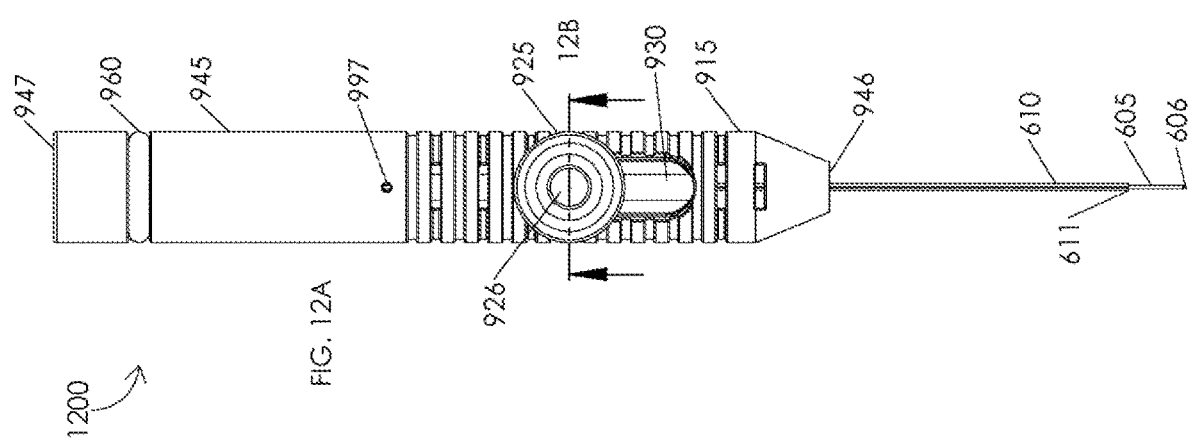

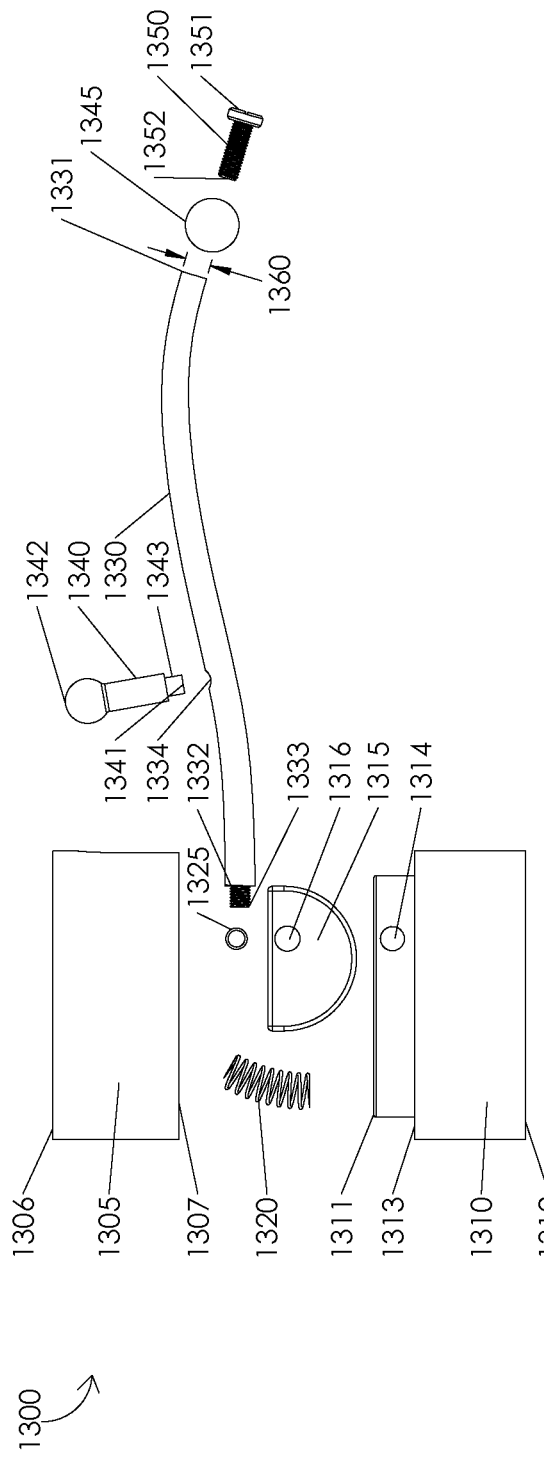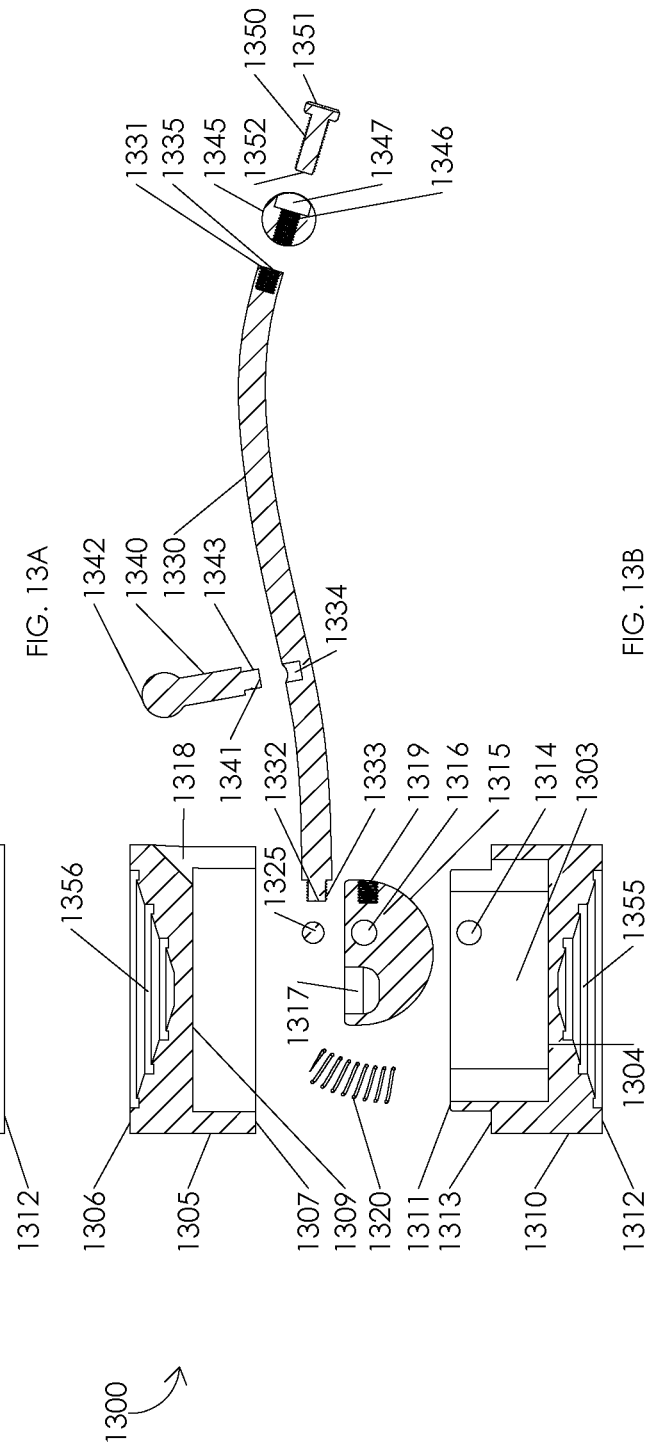

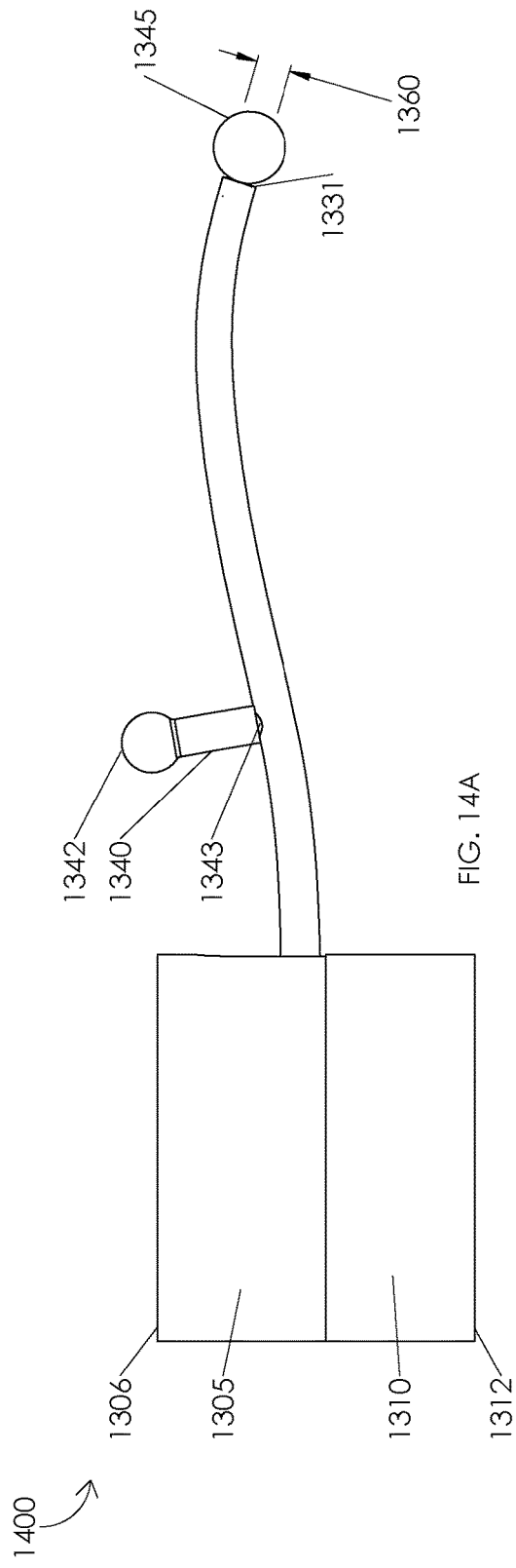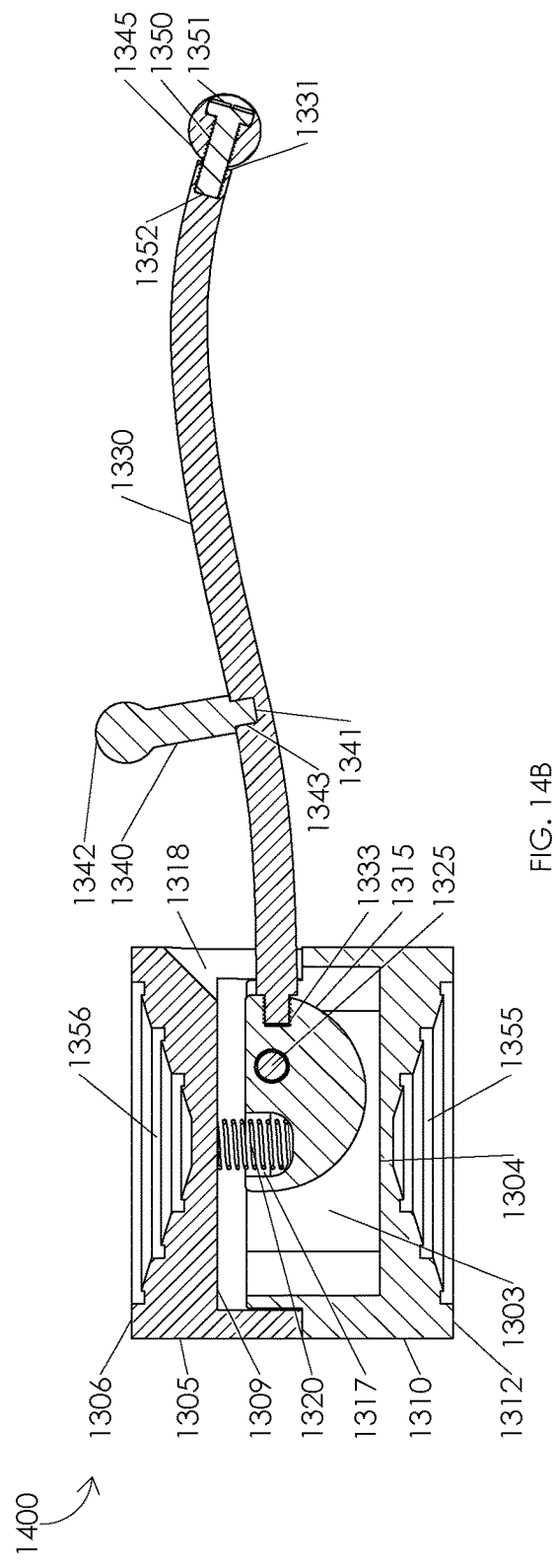

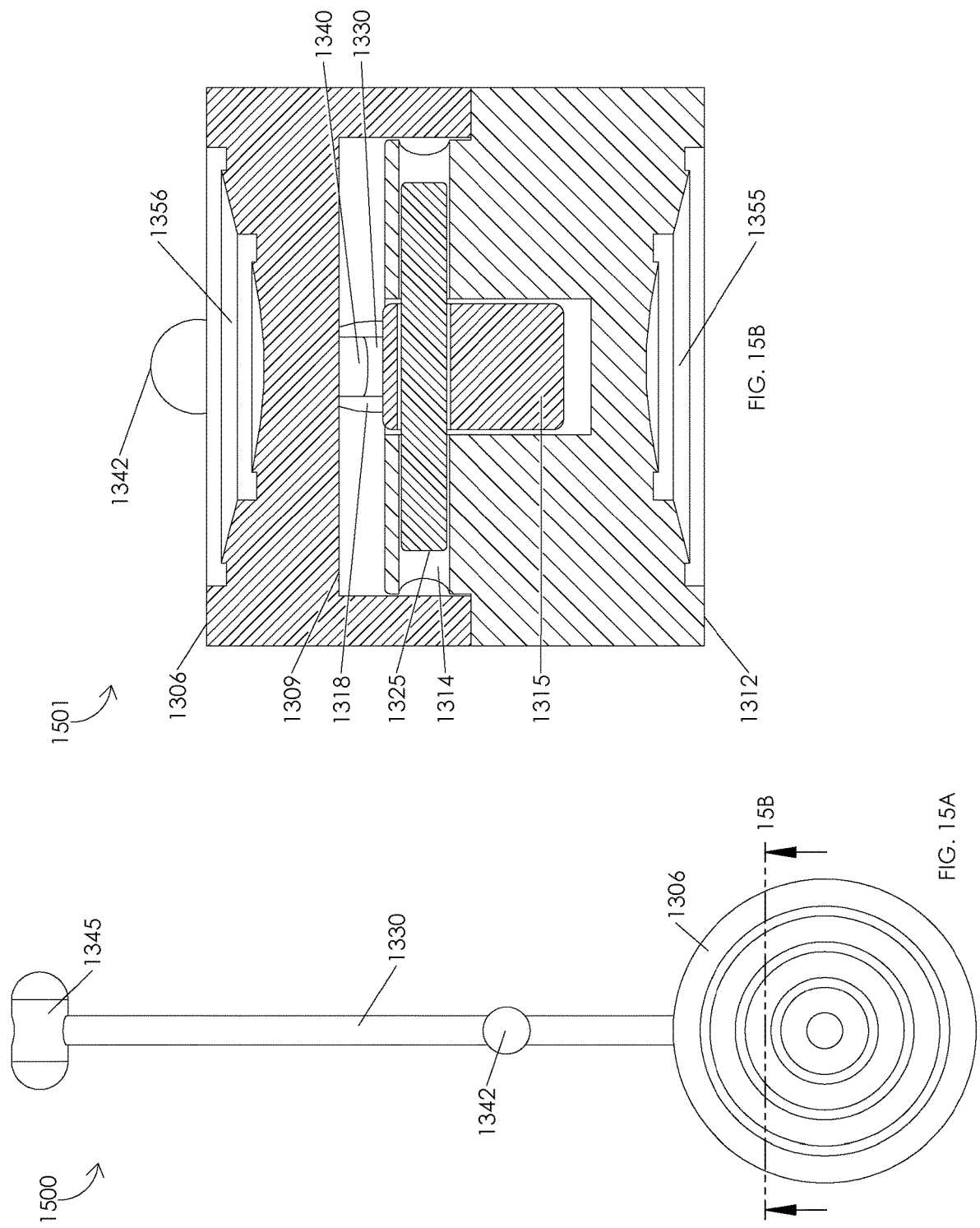

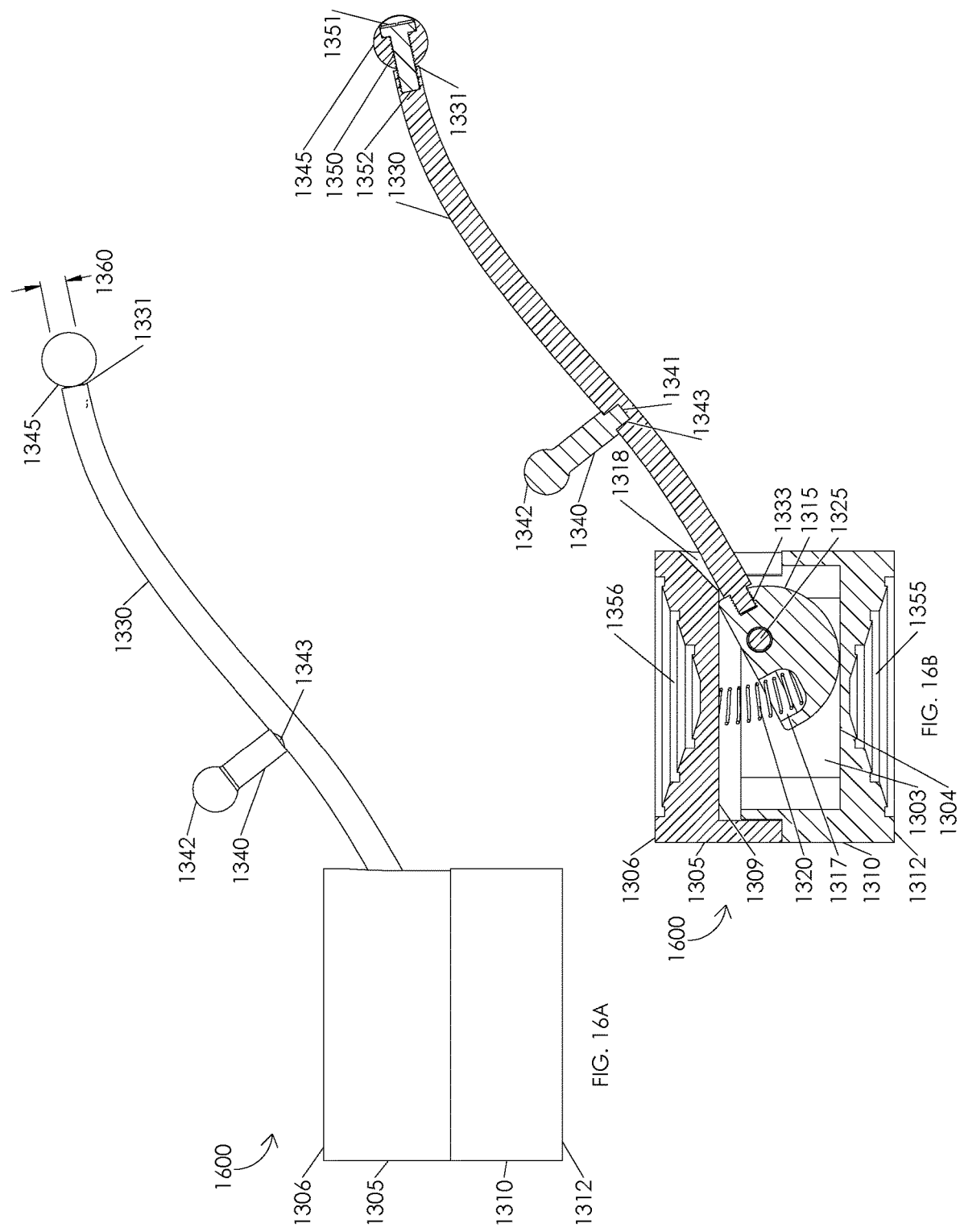

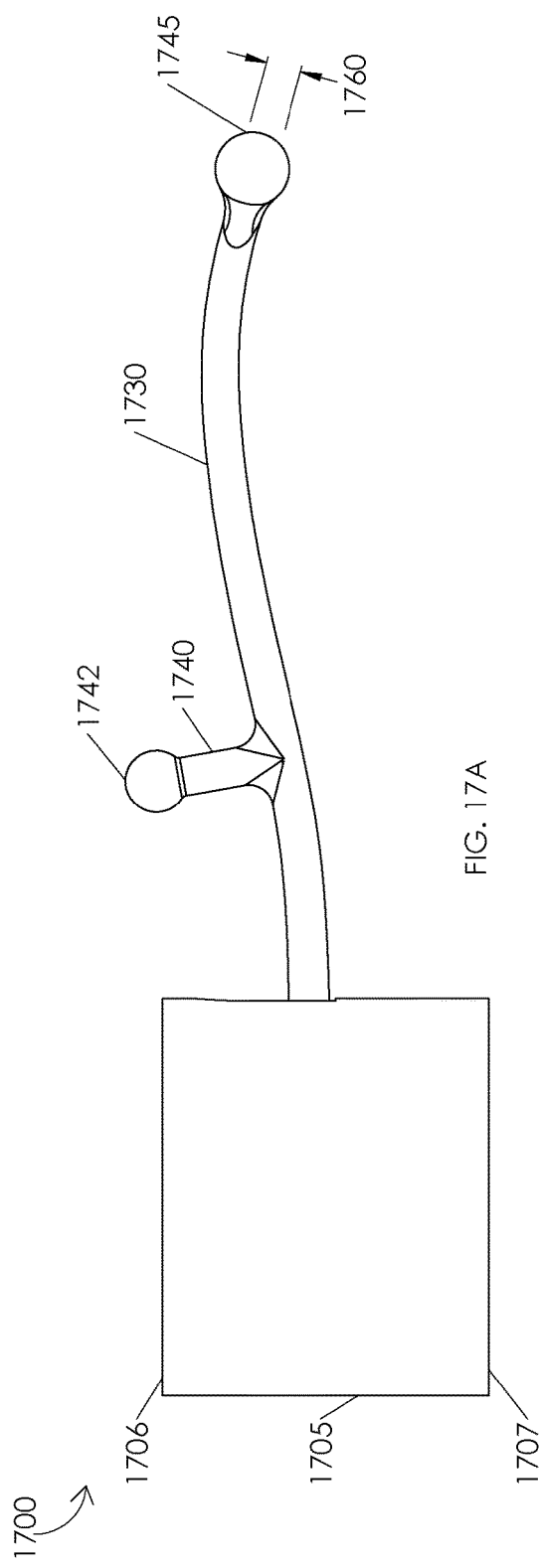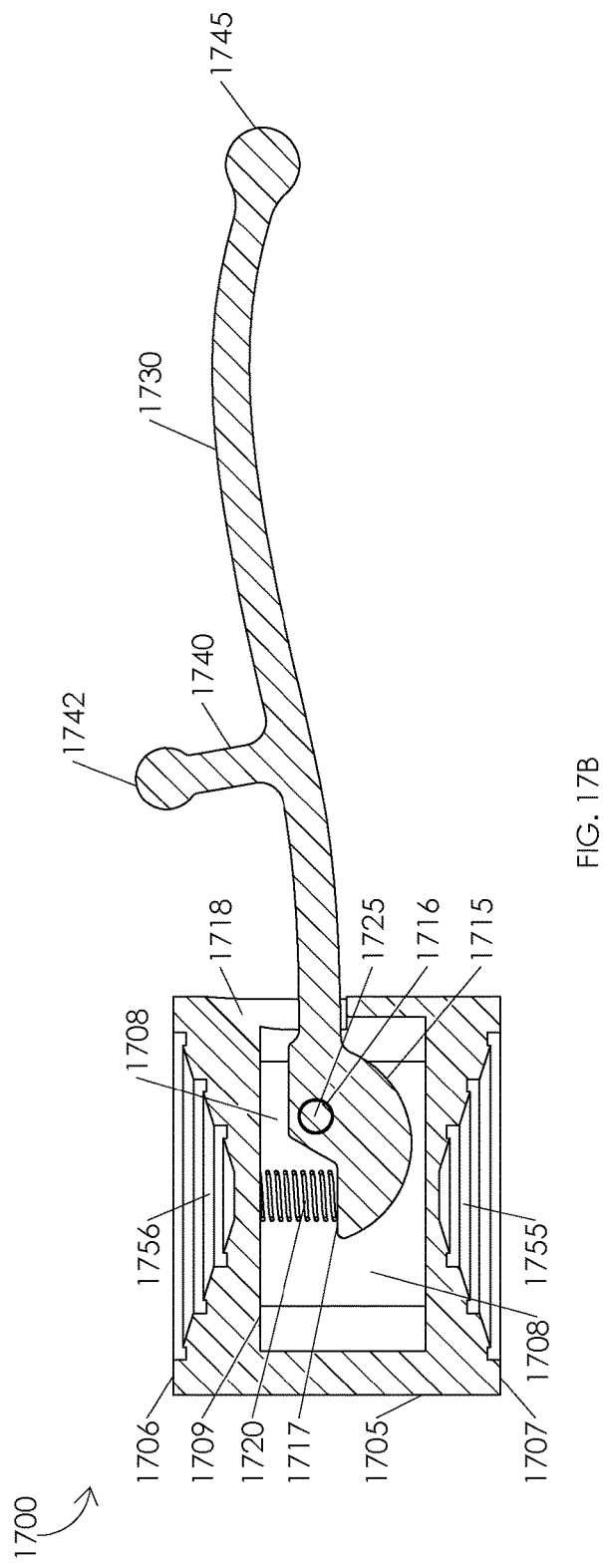

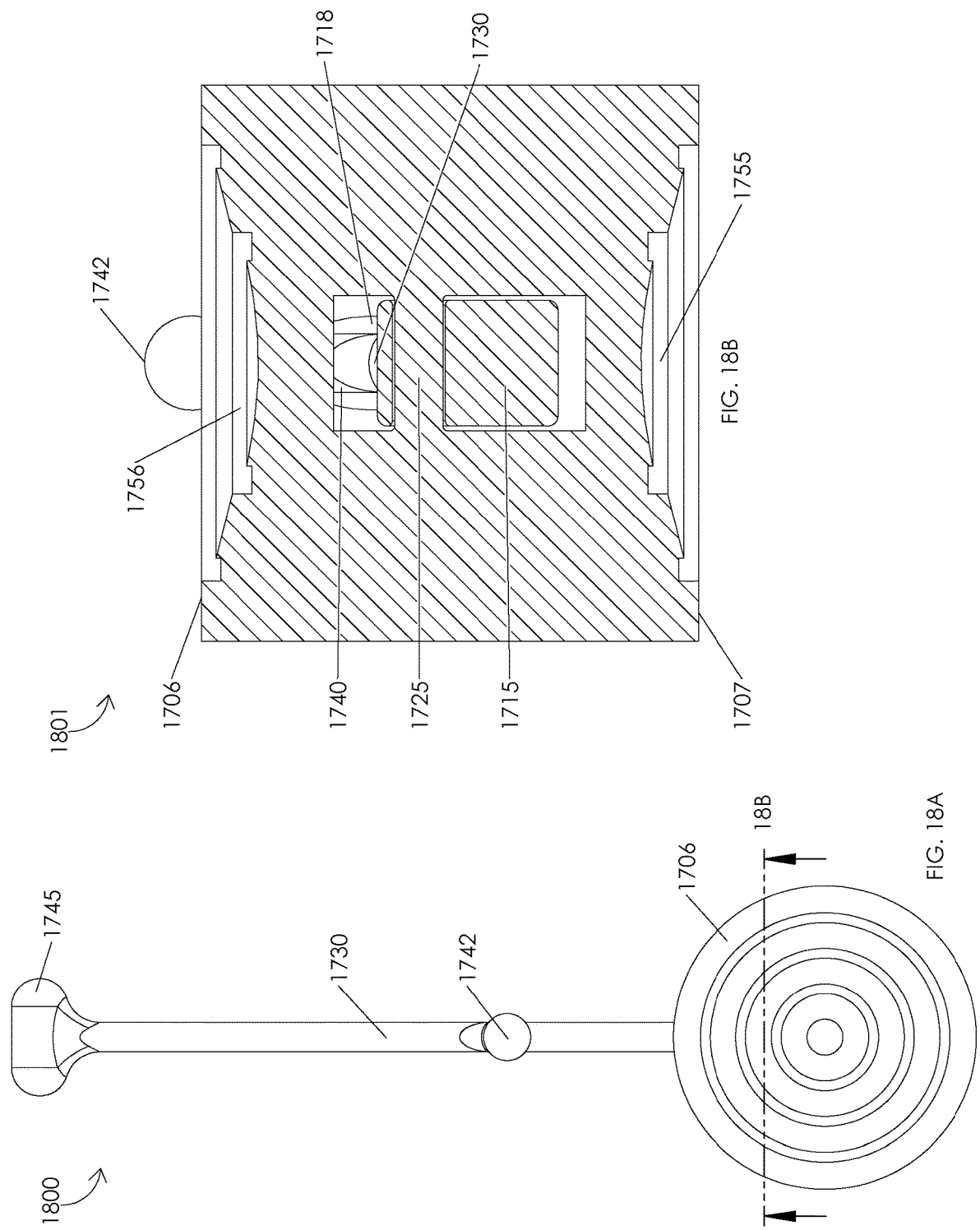

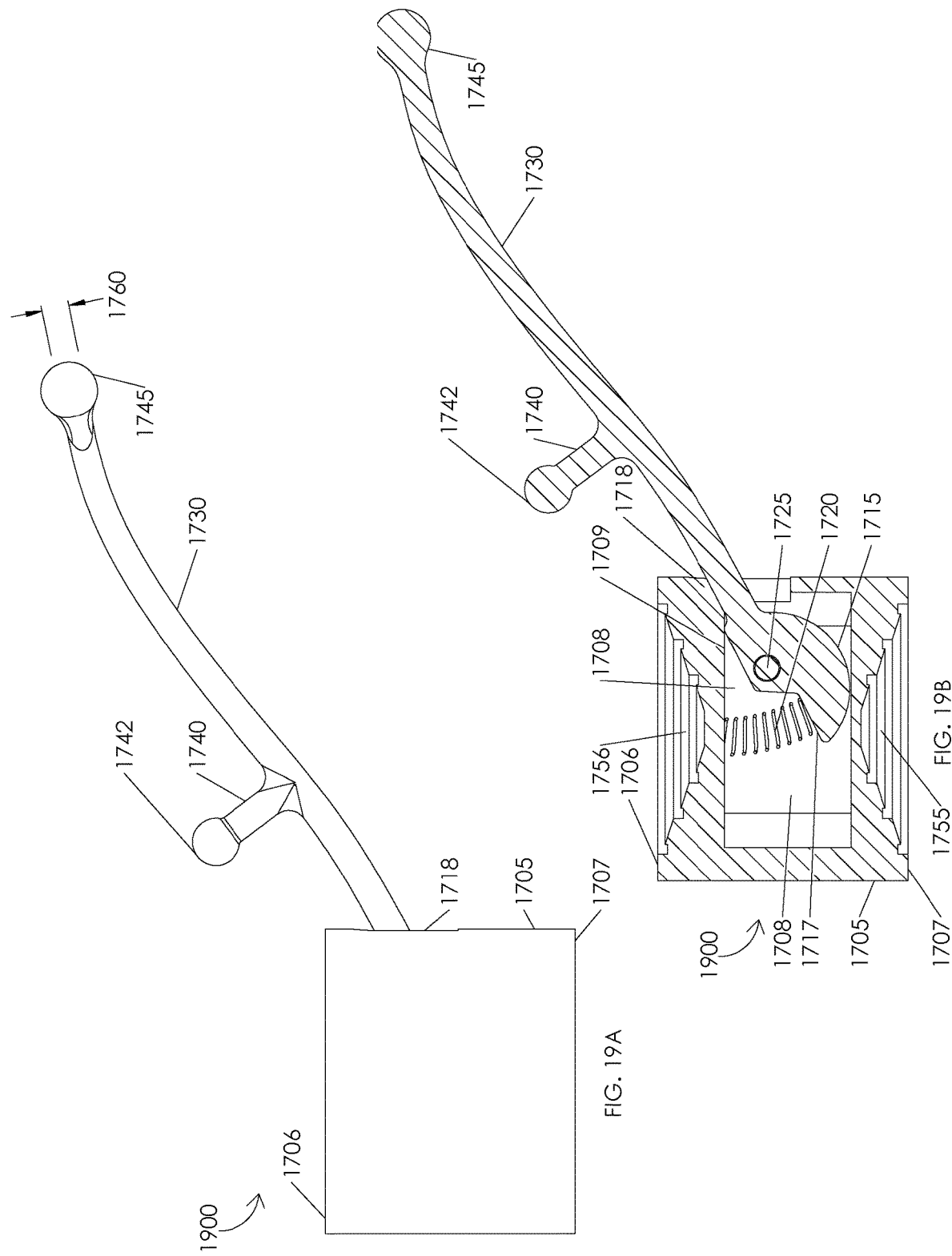

SURGICAL INSTRUMENT SUBCOMPONENT INTEGRATION BY ADDITIVE MANUFACTURING

CROSS-REFERENCE TO RELATED APPLICATIONS

This Application claims the benefit of U.S. Provisional Application No. 62/461,573, filed Feb. 21, 2017.

FIELD OF THE INVENTION

The present disclosure relates to a medical device, and, more particularly, to a surgical instrument.

BACKGROUND OF THE INVENTION

Additive manufacturing allows for fabrication of parts layer-by-layer. Most additive manufacturing processes are able to manufacture from only a single material, e.g., nylon, or manufacture from only a single type of material, e.g., polymers, metals, etc. Surgical instrument components are frequently assembled from one or more subcomponents manufactured from different materials, e.g., each of the one or more subcomponents may be manufactured by a machining process, a casting process, a molding process, a forming process, a coating process, a joining process, etc. For example, a particular surgical instrument component may be assembled from a housing subcomponent manufactured from an acetal material, a lock subcomponent manufactured from a brass material, and a spring subcomponent manufactured from a stainless steel material. Manufacturing the particular surgical instrument component from a first material by additive manufacturing may cause at least one subcomponent of the particular surgical instrument component to perform in a manner other than as intended. For example, the spring subcomponent manufactured from the first material may have a first Young's modulus and the spring subcomponent manufactured from the stainless steel material may have a second Young's modulus. Accordingly, there is a need for manufacturing a surgical instrument component by additive manufacturing without causing one or more subcomponents of the surgical instrument component to perform in a manner other than as intended.

Manufacturers of medical devices such as surgical instruments are required to comply with ISO, FDA, MEDDEV, and other regulations which require medical device manufacturers to monitor and control suppliers of subcomponents and components. Most medical device manufacturers establish such control over suppliers by conducting periodic audits of a supplier's manufacturing facility. It is common for each subcomponent of each component of a surgical instrument to have a unique supplier. In addition to the burden of regulatory compliance, each individual subcomponent and component of a surgical instrument increases a risk of nonconformance. For example, a component comprising one subcomponent having two critical features has two potential nonconformities, e.g., either one of the two critical features of the one subcomponent could fail. However, a component comprising two subcomponents wherein each of the two subcomponents has two critical features has four potential nonconformities. Accordingly, there is a need to reduce a total number of subcomponents and components of a surgical instrument.

BRIEF SUMMARY OF THE INVENTION

The present disclose provides surgical instrument subcomponent integration by additive manufacturing. In one or more embodiments, surgical instrument subcomponent integration by additive manufacturing may comprise identifying at least two subcomponents of a multi-component assembly wherein a first subcomponent of the at least two subcomponents has a first functionality and wherein the first subcomponent of the at least two subcomponents is manufactured from a first material having a first set of material properties. Illustratively, surgical instrument subcomponent integration by additive manufacturing may comprise modifying one or more properties of the first subcomponent of the at least two subcomponents to reproduce the first functionality when the first subcomponent is manufactured from a second material having a second set of material properties. In one or more embodiments, surgical instrument subcomponent integration by additive manufacturing may comprise integrating the at least two subcomponents by manufacturing an integral component by additive manufacturing wherein the integral component is manufactured from the second material and wherein the first functionality is retained.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A and 2B are schematic diagrams illustrating an assembled multi-component instrument tip;

FIGS. 3A and 3B are schematic diagrams illustrating an exploded view of a single-component instrument tip assembly;

FIGS. 4A, 4B, 5A, and 5B are schematic diagrams illustrating an assembled single-component instrument tip;

FIGS. 6A and 6B are schematic diagrams illustrating an exploded view of a multi-component laser probe assembly;

FIGS. 7A, 7B, 8A, and 8B are schematic diagrams illustrating an assembled multi-component laser probe;

FIGS. 9A and 9B are schematic diagrams illustrating an exploded view of a single-component laser probe assembly;

FIGS. 10A, 10B, 11A, 11B, 12A, and 12B are schematic diagrams illustrating an assembled single-component laser probe;

FIGS. 13A and 13B are schematic diagrams illustrating an exploded view of a multi-component scleral depressor assembly;

FIGS. 14A, 14B, 15A, 15B, 16A, and 16B are schematic diagrams illustrating an assembled multi-component scleral depressor;

FIGS. 17A, 17B, 18A, 18B, 19A, and 19B are schematic diagrams illustrating a single-component scleral depressor.

DETAILED DESCRIPTION OF AN ILLUSTRATIVE EMBODIMENT

Figure 1A:
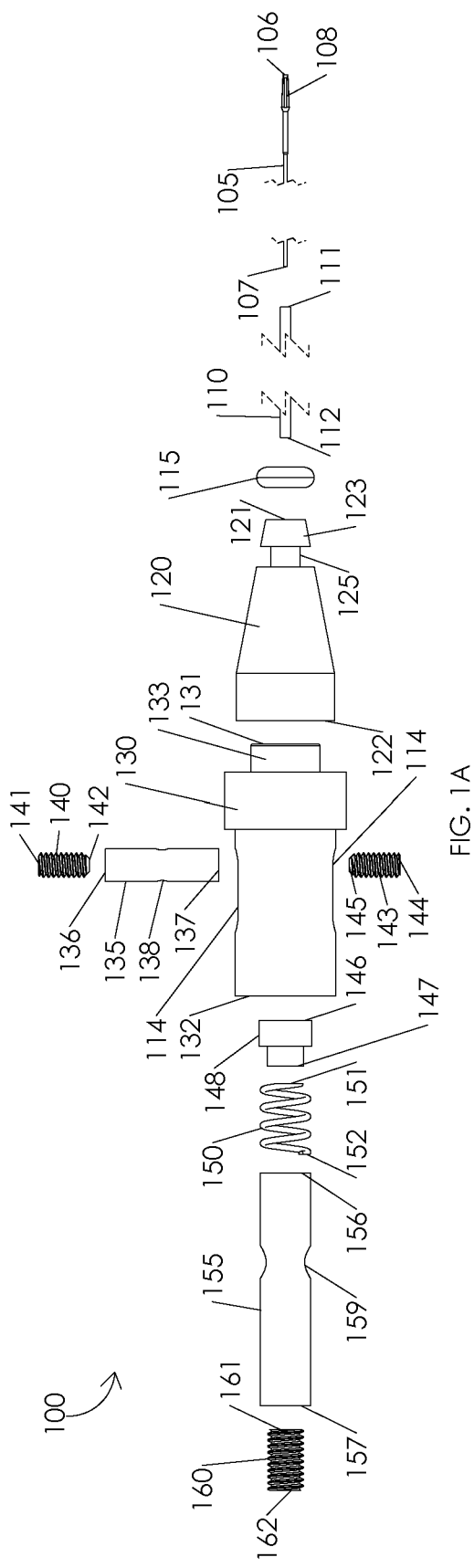
FIGS. 1A and 1B are schematic diagrams illustrating an exploded view of a multi-component instrument tip assembly.
Figure 1B:
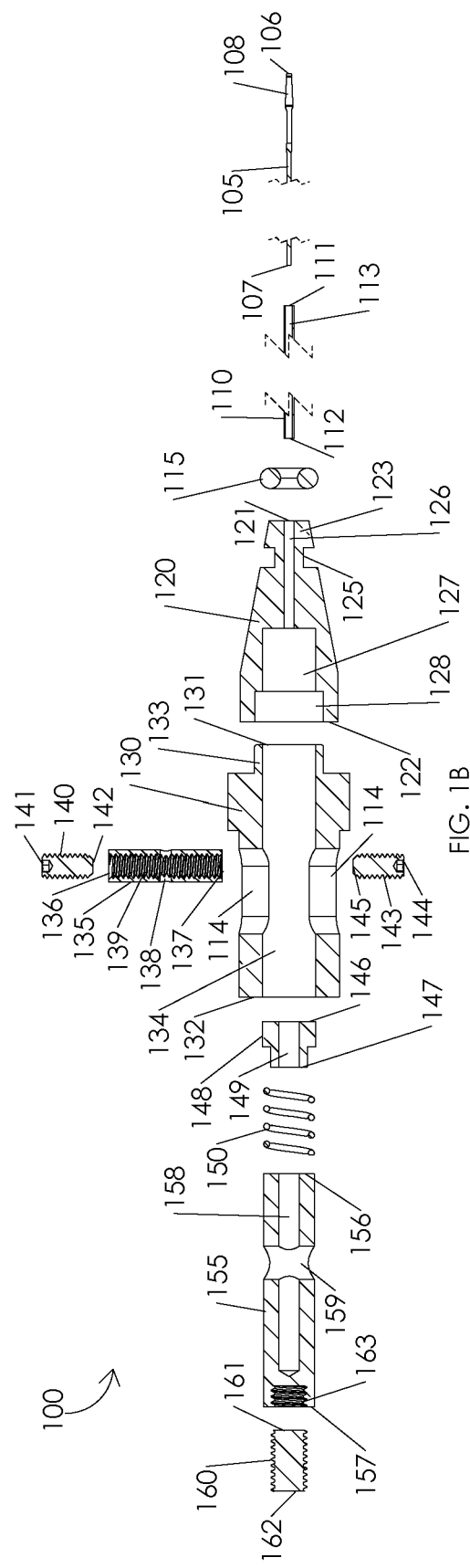

FIGS. 1A and 1B are schematic diagrams illustrating an exploded view of a multi-component instrument tip assembly 100. FIG. 1A illustrates a side view of a multi-component instrument tip assembly 100. FIG. 1B illustrates a cross-sectional view in a sagittal plane of a multi-component instrument tip assembly 100. Illustratively, a multi-component instrument tip assembly 100 may comprise a blank 105, a hypodermic tube 110, an identification ring 115, a nosecone 120, a tip base 130, a lock 135, a superior fixation mechanism 140, an inferior fixation mechanism 143, an inner nosecone 148, a spring 150, a piston 155, and a proximal fixation mechanism 160. In one or more embodiments, blank 105 may comprise a blank distal end 106, a blank proximal end 107, and a plurality of instrument jaws 108. Illustratively, blank 105 may be manufactured from any suitable material, e.g., polymers, metals, metal alloys, etc., or from any combination of suitable materials. For example, blank 105 may be manufactured by a machining process, a casting process, a molding process, a forming process, a coating process, a joining process, etc. In one or more embodiments, hypodermic tube 110 may comprise a hypodermic tube distal end 111, a hypodermic tube proximal end 112, and a hypodermic tube inner lumen 113. Illustratively, hypodermic tube 110 may be manufactured from any suitable material, e.g., polymers, metals, metal alloys, etc., or from any combination of suitable materials. For example, hypodermic tube 110 may be manufactured by a machining process, a casting process, a molding process, a forming process, a coating process, a joining process, etc. In one or more embodiments, nosecone 120 may comprise a nosecone distal end 121 and a nosecone proximal end 122. In one or more embodiments, nosecone 120 may comprise a distal taper 123 and an identification ring housing 125. Illustratively, nosecone 120 may comprise a hypodermic tube housing 126, a nosecone inner chamber 127, and a tip base housing 128. In one or more embodiments, nosecone 120 may be manufactured from any suitable material, e.g., polymers, metals, metal alloys, etc., or from any combination of suitable materials. For example, nosecone 120 may be manufactured by a machining process, a casting process, a molding process, a forming process, a coating process, a joining process, etc. Illustratively, tip base 130 may comprise a tip base distal end 131 and a tip base proximal end 132. In one or more embodiments, tip base 130 may comprise a lock guide 114, a tip base distal projection 133, and a tip base inner bore 134. Illustratively, tip base 130 may be manufactured from any suitable material, e.g., polymers, metals, metal alloys, etc., or from any combination of suitable materials. For example, tip base 130 may be manufactured by a machining process, a casting process, a molding process, a forming process, a coating process, a joining process, etc. In one or more embodiments, lock 135 may comprise a lock superior end 136 and a lock inferior end 137. Illustratively, lock 135 may comprise a medial inner bore 138 and a blank housing 139. In one or more embodiments, lock 135 may be manufactured from any suitable material, e.g., polymers, metals, metal alloys, etc., or from any combination of suitable materials. For example, lock 135 may be manufactured by a machining process, a casting process, a molding process, a forming process, a coating process, a joining process, etc. Illustratively, superior fixation mechanism 140 may comprise a superior fixation mechanism anterior end 141 and a superior fixation mechanism posterior end 142. In one or more embodiments, superior fixation mechanism 140 may be manufactured from any suitable material, e.g., polymers, metals, metal alloys, etc., or from any combination of suitable materials. For example, superior fixation mechanism 140 may be manufactured by a machining process, a casting process, a molding process, a forming process, a coating process, a joining process, etc. Illustratively, inferior fixation mechanism 143 may comprise an inferior fixation mechanism anterior end 144 and an inferior fixation mechanism posterior end 145. In one or more embodiments, inferior fixation mechanism 143 may be manufactured from any suitable material, e.g., polymers, metals, metal alloys, etc., or from any combination of suitable materials. For example, inferior fixation mechanism 143 may be manufactured by a machining process, a casting process, a molding process, a forming process, a coating process, a joining process, etc. Illustratively, inner nosecone 148 may comprise an inner nosecone distal end 146 and an inner nosecone proximal end 147. In one or more embodiments, inner nosecone 148 may comprise an inner nosecone inner bore 149. Illustratively, inner nosecone 148 may be manufactured from any suitable material, e.g., polymers, metals, metal alloys, etc., or from any combination of suitable materials. For example, inner nosecone 148 may be manufactured by a machining process, a casting process, a molding process, a forming process, a coating process, a joining process, etc. In one or more embodiments, spring 150 may comprise a spring distal end 151 and a spring proximal end 152. Illustratively, spring 150 may be manufactured from any suitable material, e.g., polymers, metals, metal alloys, etc., or from any combination of suitable materials. For example, spring 150 may be manufactured by a machining process, a casting process, a molding process, a forming process, a coating process, a joining process, etc. In one or more embodiments, piston 155 may comprise a piston distal end 156 and a piston proximal end 157. Illustratively, piston 155 may comprise a piston inner chamber 158, a piston medial chamber 159, and a proximal fixation mechanism housing 163. In one or more embodiments, piston 155 may be manufactured from any suitable material, e.g., polymers, metals, metal alloys, etc., or from any combination of suitable materials. For example, piston 155 may be manufactured by a machining process, a casting process, a molding process, a forming process, a coating process, a joining process, etc. Illustratively, proximal fixation mechanism 160 may comprise a proximal fixation mechanism distal end 161 and a proximal fixation mechanism proximal end 162. In one or more embodiments, proximal fixation mechanism 160 may be manufactured from any suitable material, e.g., polymers, metals, metal alloys, etc., or from any combination of suitable materials. For example, proximal fixation mechanism 160 may be manufactured by a machining process, a casting process, a molding process, a forming process, a coating process, a joining process, etc.

FIGS. 2A and 2B are schematic diagrams illustrating an assembled multi-component instrument tip 200. FIG. 2A illustrates a side view of an assembled multi-component instrument tip 200. FIG. 2B illustrates a cross-sectional view in a sagittal plane of an assembled multi-component instrument tip 200. In one or more embodiments, a portion of tip base 130 may be disposed in a portion of nosecone 120, e.g., tip base distal end 131 may be disposed in a portion of nosecone 120. Illustratively, tip base distal projection 133 may be disposed in tip base housing 128, e.g., tip base distal projection 133 may be fixed in tip base housing 128. In one or more embodiments, a portion of tip base 130 may be fixed in a portion of nosecone 120, e.g., a portion of tip base 130 may be fixed in a portion of nosecone 120 by an interference fit, an adhesive, a threading, a pin, a magnet, an epoxy, a weld, etc. Illustratively, inner nosecone 148 may be disco posed in nosecone 120, e.g., inner nosecone 148 may be disposed in nosecone inner chamber 128. In one or more embodiments, inner nosecone 148 may be disposed in nosecone 120 wherein inner nosecone 148 is completely disposed in nosecone 120, e.g., inner nosecone 148 may be disposed in nosecone inner chamber 128 wherein inner nosecone distal end 146 is disposed in nosecone inner chamber 128 and wherein inner nosecone proximal end 147 is disposed in nosecone inner chamber 128.

Illustratively, spring 150 may be disposed in tip base 130 and nosecone 120, e.g., spring 150 may be disposed in tip base 130 and nosecone 120 wherein spring distal end 151 is disposed in nosecone 120 and wherein spring proximal end 152 is disposed in tip base 130. In one or more embodiments, spring 150 may be disposed in nosecone 120 wherein a portion of spring 150 is disposed over a portion of inner nosecone 148, e.g., spring 150 may be disposed in nosecone 120 wherein spring distal end 151 is disposed over inner nosecone proximal end 147. In one or more embodiments, spring 150 may be disposed in nosecone 120 wherein spring distal end 151 is adjacent to a portion of inner nosecone 148, e.g., spring 150 may be disposed in nosecone 120 wherein spring distal end 151 abuts a portion of inner nosecone 148. Illustratively, piston 155 may be disposed in tip base 130 and nosecone 120, e.g., piston 155 may be disposed in tip base inner bore 134. In one or more embodiments, piston 155 may be disposed in tip base 130 wherein a portion of piston 155 extends out from a portion of tip base 130, e.g., piston 155 may be disposed in tip base inner bore 134 wherein piston proximal end 157 extends out from tip base proximal end 132. Illustratively, piston 155 may be disposed in tip base 130 wherein a portion of piston 155 is adjacent to a portion of spring 150, e.g., piston 155 may be disposed in tip base 130 wherein piston distal end 156 is adjacent to spring proximal end 152. In one or more embodiments, piston 155 may be disposed in tip base 130 wherein a portion of piston 155 abuts a portion of spring 150, e.g., piston 155 may be disposed in tip base 130 wherein piston distal end 156 abuts spring proximal end 152. Illustratively, spring 150 may be disposed between piston 155 and inner nosecone 148 wherein an actuation of piston 155 towards inner nosecone 148 is configured to compress spring 150. In one or more embodiments, spring 150 may be disposed between piston 155 and inner nosecone 148 wherein an actuation of piston 155 away from inner nosecone 148 is configured to expand spring 150.

In one or more embodiments, a portion of proximal fixation mechanism 160 may be disposed in a portion of piston 155, e.g., proximal fixation mechanism distal end 161 may be disposed in proximal fixation mechanism housing 163. Illustratively, a portion of proximal fixation mechanism 160 may be disposed in a portion of piston 155 wherein a portion of proximal fixation mechanism 160 extends out from a portion of piston 155, e.g., proximal fixation mechanism 160 may be disposed in proximal fixation mechanism housing 163 wherein proximal fixation mechanism proximal end 162 extends out from piston proximal end 157. In one or more embodiments, proximal fixation mechanism 160 may be disposed in a portion of piston 155 wherein proximal fixation mechanism 160 is fixed in piston 155, e.g., proximal fixation mechanism 160 may be fixed in piston 155 by an interference fit, an adhesive, a threading, a pin, a magnet, an epoxy, a weld, etc. In one or more embodiments, proximal fixation mechanism 160 may be configured to attach an assembled multi-component instrument tip 200 to an actuation handle (not shown). Illustratively, lock 135 may be disposed in lock guide 114 and piston medial chamber 159, e.g., lock 135 may be disposed in lock guide 114 and piston medial chamber 159 wherein medial inner bore 138 is disposed in piston inner chamber 158. In one or more embodiments, lock 135 may be disposed in lock guide 114 and piston medial chamber 159 wherein lock superior end 136 extends out from lock guide 114 and wherein lock inferior end 137 extends out from lock guide 114. Illustratively, lock 135 may be disposed in piston medial chamber 159 wherein lock 135 is fixed in piston medial chamber 159, e.g., lock 135 may be fixed in piston medial chamber 159 by an interference fit, an adhesive, a threading, a pin, a magnet, an epoxy, a weld, etc.

In one or more embodiments, superior fixation mechanism 140 may be disposed in lock 135, e.g., superior fixation mechanism 140 may be disposed in blank housing 139. Illustratively, superior fixation mechanism 140 may be fixed in blank housing 139, e.g., superior fixation mechanism 140 may be fixed in blank housing 139 by an interference fit, an adhesive, a threading, a pin, a magnet, an epoxy, a weld, etc. In one or more embodiments, inferior fixation mechanism 143 may be disposed in lock 135, e.g., inferior fixation mechanism 143 may be disposed in blank housing 139. Illustratively, inferior fixation mechanism 143 may be fixed in blank housing 139, e.g., inferior fixation mechanism 143 may be fixed in blank housing 139 by an interference fit, an adhesive, a threading, a pin, a magnet, an epoxy, a weld, etc.

In one or more embodiments, identification ring 115 may be disposed over identification ring housing 125. Illustratively, identification ring 115 may be fixed over identification ring housing 125, e.g., identification ring 115 may be fixed over identification ring housing 125 by an interference fit, an adhesive, a threading, a pin, a magnet, an epoxy, a weld, etc. In one or more embodiments, identification ring 115 may be configured to indicate one or more properties of an assembled multi-component instrument tip 200 to a user or a surgeon, e.g., identification ring 115 may be configured to indicate a type or size of cannula that is compatible with an assembled multi-component instrument tip 200. Illustratively, a portion of hypodermic tube 110 may be disposed in a portion of nosecone 120, e.g., a portion of hypodermic tube 110 may be disposed in hypodermic tube housing 126. In one or more embodiments, hypodermic tube 110 may be disposed in hypodermic tube housing 126 wherein hypodermic tube 110 is fixed in hypodermic tube housing 126, e.g., hypodermic tube 110 may be fixed in hypodermic tube housing 126 by an interference fit, an adhesive, a threading, a pin, a magnet, an epoxy, a weld, etc.

Illustratively, blank 105 may be disposed in hypodermic tube 110, e.g., blank 105 may be disposed in hypodermic tube inner lumen 113. In one or more embodiments, blank 105 may be disposed in hypodermic tube 110 wherein blank distal end 106 extends out from hypodermic tube distal end 111. Illustratively, blank 105 may be disposed in hypodermic tube 110, nosecone 120, nosecone inner chamber 127, inner nosecone 148, inner nosecone inner bore 149, spring 150, tip base 130, tip base inner bore 134, piston 155, piston inner chamber 158, piston medial chamber 159, lock 135, medial inner bore 138, and blank housing 139. In one or more embodiments, a portion of blank 105 may be fixed in blank housing 139, e.g., a portion of blank 105 may be fixed in blank housing 139 by an interference fit, an adhesive, a threading, a pin, a magnet, an epoxy, a weld, etc. In one or more embodiments, a portion of blank 105 may be fixed in blank housing 139 by superior fixation mechanism 140 and inferior fixation mechanism 143, e.g., a portion of blank 105 may be fixed between superior fixation mechanism posterior end 142 and inferior fixation mechanism posterior end 145. For example, superior fixation mechanism 140 and inferior fixation mechanism 143 may comprise setscrews configured to fix a portion of blank 105 in blank housing 139.

Illustratively, a user may employ an actuation handle (not shown) to selectively apply a force to tip base proximal end 132. In one or more embodiments, an application of a force to tip base proximal end 132 may be configured to extend tip base 130 relative to piston 155. Illustratively, an extension of tip base 130 relative to piston 155 may be configured to extend hypodermic tube 110 relative to blank 105. In one or more embodiments, an extension of hypodermic tube 110 relative to blank 105 may be configured to close instrument jaws 108. Illustratively, spring 150 may be configured to provide a force that resists an extension of hypodermic tube 110 relative to blank 105.

Illustratively, a user may employ an actuation handle (not shown) to selectively reduce or remove a force applied to tip base proximal end 132. In one or more embodiments, a reduction or a removal of a force applied to tip base proximal end 132 may be configured to retract tip base 130 relative to piston 155. Illustratively, a retraction of tip base 130 relative to piston 155 may be configured to retract hypodermic tube 110 relative to blank 105. In one or more embodiments, a retraction of hypodermic tube 110 relative to blank 105 may be configured to open instrument jaws 108. Illustratively, spring 150 may be configured to provide a force that facilitates a retraction of hypodermic tube 110 relative to blank 105.

FIGS. 3A and 3B are schematic diagrams illustrating an exploded view of a single-component instrument tip assembly 300. FIG. 3A illustrates a side view of a single-component instrument tip assembly 300. FIG. 3B illustrates a cross-sectional view in a sagittal plane of a single-component instrument tip assembly 300. In one or more embodiments, a single-component instrument tip assembly 300 may comprise a blank 105, a hypodermic tube 110, and a single-component tip base 320. Illustratively, blank 105 may comprise a blank distal end 106 and a blank proximal end 107. In one or more embodiments, blank 105 may comprise a plurality of instrument jaws 108. Illustratively, blank 105 may be manufactured from any suitable material, e.g., polymers, metals, metal alloys, etc., or from any combination of suitable materials. In one or more embodiments, hypodermic tube 110 may comprise a hypodermic tube distal end 111 and a hypodermic tube proximal end 112. Illustratively, hypodermic tube 110 may comprise a hypodermic tube inner lumen 113. In one or more embodiments, hypodermic tube 110 may be manufactured from any suitable material, e.g., polymers, metals, metal alloys, etc., or from any combination of suitable materials.

Illustratively, single-component tip base 320 may comprise a single-component tip base distal end 321 and a single-component tip base proximal end 322. In one or more embodiments, single-component tip base 320 may comprise an integral identification ring 315. Illustratively, single-component tip base 320 may comprise a flange 323. In one or more embodiments, single-component tip base 320 may comprise a tip protector interface 330. Illustratively, single-component tip base 320 may comprise a spring housing 334. For example, single-component tip base 320 may comprise an integral hypodermic tube housing 363. In one or more embodiments, single-component tip base 320 may comprise an integral actuation mechanism 335. Illustratively, integral actuation mechanism 335 may comprise an integral actuation mechanism superior end 336 and an integral actuation mechanism inferior end 337. In one or more embodiments, integral actuation mechanism 335 may comprise an integral actuation mechanism inner chamber 339. Illustratively, single-component tip base 320 may comprise an integral fixation mechanism 340. In one or more embodiments, single-component tip base 320 may comprise a distal chamber 349. Illustratively, single-component tip base 320 may comprise an integral spring 350. In one or more embodiments, single-component tip base 320 an integral extension mechanism 355. Illustratively, integral extension mechanism 355 may comprise an integral extension mechanism distal end 356 and an integral extension mechanism proximal end 357. In one or more embodiments, single-component tip base 320 may comprise a proximal chamber 358. Illustratively, single-component tip base 320 may comprise an integral proximal fixation mechanism 360. In one or more embodiments, integral proximal fixation mechanism 360 may comprise an integral proximal fixation mechanism proximal end 362. Illustratively, single-component tip base 320 may comprise a snap-fit release member 370. In one or more embodiments, single-component tip base 320 may comprise a snap-fit release guide 371. Illustratively, single-component tip base 320 may comprise a first limb lock housing 372. In one or more embodiments, single-component tip base 320 may comprise a first snap-fit limb lock 373. Illustratively, single-component tip base 320 may comprise a second limb lock housing 374. In one or more embodiments, single-component tip base 320 may comprise a second snap-fit limb lock 375. Illustratively, single-component tip base 320 may comprise a snap-fit limb joint 380. In one or more embodiments, single-component tip base 320 may comprise a first snap-fit limb 381. Illustratively, single-component tip base 320 may comprise a second snap-fit limb 382. In one or more embodiments, single-component tip base 320 may comprise a snap-fit limb housing 385. Illustratively, one or more portions of single-component tip base 320 may be manufactured by additive manufacturing, e.g., one or more portions of single-component tip base 320 may be manufactured by selective laser sintering, selective heat sintering, selective laser melting, electron-beam melting, direct metal laser sintering, electron beam freeform fabrication, stereolithography, digital light processing, fused deposition modeling, laminated object manufacturing, ultrasonic additive manufacturing, vat photopolymerization, material jetting, binder jetting, laser engineered net shaping, etc. In one or more embodiments, single-component tip base 320 may be manufactured entirely by additive manufacturing, e.g., single-component tip base 320 may be manufactured entirely by selective laser sintering, selective heat sintering, selective laser melting, electron-beam melting, direct metal laser sintering, electron beam freeform fabrication, stereolithography, digital light processing, fused deposition modeling, laminated object manufacturing, ultrasonic additive manufacturing, vat photopolymerization, material jetting, binder jetting, laser engineered net shaping, etc. For example, single-component tip base 320 may be manufactured by selective laser sintering from a nylon material.

FIGS. 4A, 4B, 5A, and 5B are schematic diagrams illustrating an assembled single-component instrument tip 400. FIG. 4A illustrates a side view of an assembled single-component instrument tip 400. FIG. 4B illustrates a cross-sectional view in a sagittal plane of an assembled single-component instrument tip 400. FIG. 5A illustrates an inferior view of an assembled single-component instrument tip 500. FIG. 5B illustrates a cross-sectional view in a frontal plane of an assembled single-component instrument tip 501. Illustratively, a portion of hypodermic tube 110 may be disposed in a portion of single-component tip base 320, e.g., hypodermic tube proximal end 112 may be disposed in flange 323. In one or more embodiments, a portion of hypodermic tube 110 may be fixed in a portion of single-component tip base 320, e.g., a portion of hypodermic tube 110 may be fixed in a portion of single-component tip base 320 by an interference fit, an adhesive, a threading, a pin, a magnet, an epoxy, a weld, etc. Illustratively, a portion of hypodermic tube 110 may be disposed in integral hypodermic tube housing 363, e.g., housing tube proximal end 112 may be disposed in integral hypodermic tube housing 363. In one or more embodiments, a portion of hypodermic tube 110 may be fixed in integral hypodermic tube housing 363, e.g., a portion of hypodermic tube 110 may be fixed in integral hypodermic tube housing 363 by an interference fit, an adhesive, a threading, a pin, a magnet, an epoxy, a weld, etc. Illustratively, blank 105 may be disposed in hypodermic tube 110, e.g., blank 105 may be disposed in hypodermic tube inner lumen 113. In one or more embodiments, blank 105 may be disposed in hypodermic tube 110, distal chamber 349, spring housing 334, integral spring 350, integral actuation mechanism 335, integral actuation mechanism inner chamber 339, integral fixation mechanism 440, and proximal chamber 358.

Illustratively, blank 105 may be fixed in integral fixation mechanism 340, e.g., blank 105 may be fixed in integral fixation mechanism 340 by an interference fit, an adhesive, a threading, a pin, a magnet, an epoxy, a weld, etc. In one or more embodiments, blank 105 may be fixed in integral fixation mechanism 340 by a snap-fit. Illustratively, blank 105 may be disposed between first snap-fit limb 381 and second snap-fit limb 382 wherein first snap-fit limb 381 and second snap-fit limb 382 fix blank 105 in integral fixation mechanism 340. In one or more embodiments, blank 105 may be disposed inferior to snap-fit limb joint 380, e.g., blank 105 may be disposed between snap-fit limb joint 380 and snap-fit limb housing 385. Illustratively, first snap-fit limb 381 may be disposed between blank 105 and snap-fit release guide 371. In one or more embodiments, second snap-fit limb 382 may be disposed between blank 105 and snap-fit release guide 371. Illustratively, first snap-fit limb 381 may be disposed in snap-fit limb housing 385, e.g., first snap-fit limb 381 may be fixed in snap-fit limb housing 385. In one or more embodiments, first snap-fit limb 381 may be fixed in snap-fit limb housing 385 by first snap-fit limb lock 373, e.g., first snap-fit limb lock 373 may be disposed in first limb lock housing 372. Illustratively, second snap-fit limb 382 may be disposed in snap-fit limb housing 385, e.g., second snap-fit limb 382 may be fixed in snap-fit limb housing 385. In one or more embodiments, second snap-fit limb 381 may be fixed in snap-fit limb housing 385 by second snap-fit limb lock 375, e.g., second snap-fit limb lock 375 may be disposed in second limb lock housing 374. Illustratively, a user may free blank 105 from integral fixation mechanism 340, e.g., a user may grasp snap-fit release member 370 and apply a force vector to snap-fit release member 370 directed away from snap-fit limb housing 385. In one or more embodiments, as a force vector directed away from snap-fit limb housing 385 is applied to snap-fit release member 370, snap-fit release guide 371 may be configured to cause first snap-fit limb 381 to actuate towards second snap-fit limb 382 and actuate first snap-fit limb lock 373 out from first limb lock housing 372. Illustratively, as a force vector directed away from snap-fit limb housing 385 is applied to snap-fit release member 385, snap-fit release guide 371 may be configured to cause second snap-fit limb 382 to actuate towards first snap-fit limb 381 and actuate second snap-fit limb lock 375 out from second limb lock housing 374. In one or more embodiments, an actuation of first snap-fit limb lock 373 out from first limb lock housing 372 and an actuation of second snap-fit limb lock 375 out from second limb lock housing 374 may be configured to free blank 105 from integral fixation mechanism 340.

Illustratively, a user may employ an actuation handle (not shown) to selectively apply a force to single-component tip base proximal end 322. In one or more embodiments, an application of a force to single-component tip base proximal end 322 may be configured to extend single-component tip base distal end 321 relative to integral actuation mechanism 335. Illustratively, an extension of tip base single-component tip base distal end 321 relative to integral actuation mechanism 335 may be configured to extend hypodermic tube 110 relative to blank 105. In one or more embodiments, an extension of hypodermic tube 110 relative to blank 105 may be configured to close instrument jaws 108. Illustratively, integral spring 350 may be configured to provide a force that resists an extension of hypodermic tube 110 relative to blank 105.

Illustratively, a user may employ an actuation handle (not shown) to selectively reduce or remove a force applied to single-component tip base proximal end 322. In one or more embodiments, a reduction or a removal of a force applied to single-component tip base proximal end 322 may be configured to retract single-component tip base distal end 321 relative to integral actuation mechanism 335. Illustratively, a retraction of single-component tip base distal end 321 relative to integral actuation mechanism 335 may be configured to retract hypodermic tube 110 relative to blank 105. In one or more embodiments, a retraction of hypodermic tube 110 relative to blank 105 may be configured to open instrument jaws 108. Illustratively, integral spring 350 may be configured to provide a force that facilitates a retraction of hypodermic tube 110 relative to blank 105. In one or more embodiments, integral identification ring 315 may be configured to indicate one or more properties of an assembled single-component instrument tip 400 to a user or a surgeon, e.g., integral identification ring 315 may be configured to indicate a type or size of cannula that is compatible with an assembled single-component instrument tip 400. Illustratively, integral proximal fixation mechanism 360 may be configured to attach an assembled single-component instrument tip 400 to an actuation handle (not shown).

In one or more embodiments, single-component tip base 320 may be manufactured by additive manufacturing wherein one or more subcomponents of a multi-component instrument tip assembly 100 are eliminated but a functionality of the one or more subcomponents is retained, e.g., single-component tip base 320 eliminates nosecone 120 and tip base 130 as subcomponents but retains a functionality of housing hypodermic tube 110 and integral spring 350. Illustratively, integral identification ring 315 may be manufactured by additive manufacturing wherein one or more subcomponents of a multi-component instrument tip assembly 100 are eliminated but a functionality of the one or more subcomponents is retained, e.g., integral identification ring 315 eliminates identification ring 115 as a subcomponent but retains a functionality of indicating one or more properties of an assembled single-component instrument tip 400 to a user or a surgeon. In one or more embodiments, integral fixation mechanism 340 may be manufactured by additive manufacturing wherein one or more subcomponents of a multi-component instrument tip assembly 100 are eliminated but a functionality of the one or more subcomponents is retained, e.g., integral fixation mechanism 340 eliminates lock 135, superior fixation mechanism 140 and inferior fixation mechanism 143 as subcomponents but retains a functionality of fixing blank 105 in integral fixation mechanism 340. Illustratively, integral actuation mechanism 335 may be manufactured by additive manufacturing wherein one or more subcomponents of a multi-component instrument tip assembly 100 are eliminated but a functionality of the one or more subcomponents is retained, e.g., integral actuation mechanism 335 eliminates piston 155 as a subcomponent but retains a functionality of facilitating an actuation of hypodermic tube 110 relative to blank 105. For example, integral actuation mechanism 335 may be manufactured by additive manufacturing wherein integral actuation mechanism 335 eliminates lock 135 as a subcomponent of a multi-component instrument tip assembly 100 but retains a functionality of housing integral fixation mechanism 340. In one or more embodiments, integral proximal fixation mechanism 360 may be manufactured by additive manufacturing wherein one or more subcomponents of a multi-component instrument tip assembly 100 are eliminated but a functionality of the one or more subcomponents is retained, e.g., integral proximal fixation mechanism 360 eliminates proximal fixation mechanism 160 as a subcomponent but retains a functionality of attaching an assembled single-component instrument tip 400 relative to an actuation handle (not shown). Illustratively, integral spring 350 may be manufactured by additive manufacturing wherein one or more subcomponents of a multi-component instrument tip assembly 100 are eliminated but a functionality of the one or more subcomponents is retained, e.g., integral spring 350 eliminates spring 150 as a subcomponent but retains a functionality of providing a force to resist an extension of hypodermic tube 110 relative to blank 105 and providing a force to facilitate a retraction of hypodermic tube 110 relative to blank 105. In one or more embodiments, integral extension mechanism 355 may be manufactured by additive manufacturing wherein one or more subcomponents of a multi-component instrument tip assembly 100 are eliminated but a functionality of the one or more subcomponents is retained, e.g., integral extension mechanism 355 may eliminate piston 155 as a subcomponent but retains a functionality of facilitating an actuation of hypodermic tube 110 relative to blank 105.

FIGS. 6A and 6B are schematic diagrams illustrating an exploded view of a multi-component laser probe assembly 600. FIG. 6A illustrates a side view of a multi-component laser probe assembly 600. FIG. 6B illustrates a cross-sectional view in a sagittal plane of a multi-component laser probe assembly 600. In one or more embodiments, a multi-component laser probe assembly 600 may comprise a housing tube 605, a housing tube sleeve 610, a laser probe nosecone 615, a laser probe distal fixation mechanism 620, a control mechanism 625, a piston tube 630, a piston tube housing 635, a hermetic seal ring 640, a handle base 645, a laser probe proximal fixation mechanism 650, and a laser probe identification ring 660.

Illustratively, housing tube 605 may comprise a housing tube distal end 606 and a housing tube proximal end 607. In one or more embodiments, housing tube 605 may comprise a housing tube inner diameter 607. Illustratively, housing tube 605 may be manufactured from any suitable material, e.g., polymers, metals, metal alloys, etc., or from any combination of suitable materials. For example, housing tube 605 may be manufactured by a machining process, a casting process, a molding process, a forming process, a coating process, a joining process, etc. In one or more embodiments, housing tube sleeve 610 may comprise a housing tube sleeve distal end 611 and a housing tube sleeve proximal end 612. Illustratively, housing tube sleeve 610 may comprise a housing tube sleeve inner diameter 613. In one or more embodiments, housing tube sleeve 610 may be manufactured from any suitable material, e.g., polymers, metals, metal alloys, etc., or from any combination of suitable materials. For example, housing tube sleeve 610 may be manufactured by a machining process, a casting process, a molding process, a forming process, a coating process, a joining process, etc. Illustratively, laser probe nosecone 615 may comprise a laser probe nosecone distal end 616 and a laser probe nosecone proximal end 617. In one or more embodiments, laser probe nosecone 615 may comprise a threading 618. Illustratively, laser probe nosecone 615 may comprise a housing tube sleeve guide 665. In one or more embodiments, laser probe nosecone 615 may comprise a piston tube guide 666. Illustratively, laser probe nosecone 615 may be manufactured from any suitable material, e.g., polymers, metals, metal alloys, etc., or from any combination of suitable materials. For example, laser probe nosecone 615 may be manufactured by a machining process, a casting process, a molding process, a forming process, a coating process, a joining process, etc. In one or more embodiments, laser probe distal fixation mechanism 620 may comprise a laser probe distal fixation mechanism superior end 621 and a laser probe distal fixation mechanism inferior end 622. Illustratively, laser probe distal fixation mechanism 620 may be manufactured from any suitable material, e.g., polymers, metals, metal alloys, etc., or from any combination of suitable materials. For example, laser probe distal fixation mechanism 620 may be manufactured by a machining process, a casting process, a molding process, a forming process, a coating process, a joining process, etc.

In one or more embodiments, control mechanism 625 may comprise a control mechanism superior end 626 and a control mechanism inferior end 627. Illustratively, control mechanism 625 may comprise a control mechanism base 628. In one or more embodiments, control mechanism 625 may comprise a control mechanism inner bore 629. Illustratively, control mechanism 625 may comprise a control mechanism inner chamber 670. In one or more embodiments, control mechanism 625 may be manufactured from any suitable material, e.g., polymers, metals, metal alloys, etc., or from any combination of suitable materials. For example, control mechanism 625 may be manufactured by a machining process, a casting process, a molding process, a forming process, a coating process, a joining process, etc. Illustratively, piston tube 630 may comprise a piston tube distal end 631 and a piston tube proximal end 632. In one or more embodiments, piston tube 630 may comprise a piston tube inner lumen 675. Illustratively, piston tube 630 may be manufactured from any suitable material, e.g., polymers, metals, metal alloys, etc., or from any combination of suitable materials. For example, piston tube 630 may be manufactured by a machining process, a casting process, a molding process, a forming process, a coating process, a joining process, etc. In one or more embodiments, piston tube housing 635 may comprise a piston tube housing distal end 636 and a piston tube housing proximal end 637. Illustratively, piston tube housing 635 may comprise a laser probe proximal fixation mechanism housing 638. In one or more embodiments, piston tube housing 635 may comprise a piston tube receptacle 680. Illustratively, piston tube housing 635 may comprise a housing tube guide 681. In one or more embodiments, piston tube housing 635 may comprise an optic fiber guide 682. Illustratively, piston tube housing 635 may comprise a proximal taper 683. In one or more embodiments, piston tube housing 635 may be manufactured from any suitable material, e.g., polymers, metals, metal alloys, etc., or from any combination of suitable materials. For example, piston tube housing 635 may be manufactured by a machining process, a casting process, a molding process, a forming process, a coating process, a joining process, etc.

Illustratively, hermetic seal ring 640 may be configured to establish a hermetic seal in a portion of handle base 645. In one or more embodiments, hermetic seal ring 640 may be manufactured from any suitable material, e.g., polymers, metals, metal alloys, etc., or from any combination of suitable materials. For example, hermetic seal ring 640 may be manufactured by a machining process, a casting process, a molding process, a forming process, a coating process, a joining process, etc. Illustratively, handle base 645 may comprise a handle base distal end 646 and a handle base proximal end 647. In one or more embodiments, handle base 645 may comprise a laser probe identification ring housing 648. Illustratively, handle base 645 may comprise a laser probe proximal fixation mechanism chamber 649. In one or more embodiments, handle base 645 may comprise a threading housing 685. Illustratively, handle base 645 may comprise a control mechanism guide 686. In one or more embodiments, handle base 645 may comprise a piston tube housing receptacle 687. Illustratively, handle base 645 may comprise a handle base inner bore 688. In one or more embodiments, handle base 645 may comprise a connector distal housing 689. Illustratively, handle base 645 may comprise a connector medial housing 690. In one or more embodiments, handle base 645 may comprise a connector proximal housing 691. Illustratively, handle base 645 may be manufactured from any suitable material, e.g., polymers, metals, metal alloys, etc., or from any combination of suitable materials. For example, handle base 645 may be manufactured by a machining process, a casting process, a molding process, a forming process, a coating process, a joining process, etc. In one or more embodiments, laser probe proximal fixation mechanism 650 may comprise a laser probe proximal fixation mechanism superior end 651 and a laser probe proximal fixation mechanism inferior end 652. Illustratively, laser probe proximal fixation mechanism 650 may be manufactured from any suitable material, e.g., polymers, metals, metal alloys, etc., or from any combination of suitable materials. For example, laser probe proximal fixation mechanism 650 may be manufactured by a machining process, a casting process, a molding process, a forming process, a coating process, a joining process, etc. In one or more embodiments, laser probe identification ring 660 may be configured to indicate one or more properties of an assembled multi-component laser probe to a user or a surgeon, e.g., laser probe identification ring 660 may be configured to indicate a type or size of cannula that is compatible with an assembled multi-component laser probe. Illustratively, laser probe identification ring 660 may be manufactured from any suitable material, e.g., polymers, metals, metal alloys, etc., or from any combination of suitable materials. For example, laser probe identification ring 660 may be manufactured by a machining process, a casting process, a molding process, a forming process, a coating process, a joining process, etc.

FIGS. 7A, 7B, 8A, and 8B are schematic diagrams illustrating an assembled muftis component laser probe. FIG. 7A illustrates a side view of an assembled multi-component laser probe with a curved housing tube 700. FIG. 7B illustrates a cross-sectional view in a sagittal plane of an assembled multi-component laser probe with a curved housing tube 700. FIG. 8A illustrates a side view of an assembled multi-component laser probe with a straightened housing tube 800. FIG. 8B illustrates a cross-sectional view in a sagittal plane of an assembled multi-component laser probe with a straightened housing tube 800. Illustratively, laser probe identification ring 660 may be disposed in laser probe identification ring housing 648. In one or more embodiments, laser probe identification ring 660 may be fixed in laser probe identification ring housing 448, e.g., laser probe identification ring 660 may be fixed in laser probe identification ring housing 448 by an interference fit, an adhesive, a threading, a pin, a magnet, an epoxy, a weld, etc. Illustratively, hermetic seal ring 640 may be disposed in handle base 645, e.g., hermetic seal ring 640 may be disposed in handle base 645 wherein hermetic seal ring 640 is disposed between piston tube housing receptacle 687 and handle base inner bore 688. In one or more embodiments, hermetic seal ring 640 may be fixed in handle base 645, e.g., hermetic seal ring 640 may be fixed in handle base 645 by an interference fit, an adhesive, a threading, a pin, a magnet, an epoxy, a weld, etc.

Illustratively, piston tube housing 635 may be disposed in handle base 645, e.g., piston tube housing 635 may be disposed in piston tube housing receptacle 687. Illustratively, piston tube housing 635 may be fixed in piston tube housing receptacle 687, e.g., piston tube housing 635 may be fixed in piston tube housing receptacle 687 by an interference fit, an adhesive, a threading, a pin, a magnet, an epoxy, a weld, etc. In one or more embodiments, piston tube 635 may be fixed in piston tube housing receptacle 687 by laser probe proximal fixation mechanism 650. Illustratively, laser probe proximal fixation mechanism 650 may be disposed in laser probe proximal fixation mechanism chamber 649 and laser probe proximal fixation mechanism housing 638, e.g., laser probe proximal fixation mechanism 650 may be disposed in laser probe proximal fixation mechanism chamber 649 and laser probe proximal fixation mechanism housing 638 wherein laser probe proximal fixation mechanism superior end 651 is disposed in laser probe proximal fixation mechanism chamber 649 and wherein laser probe proximal fixation mechanism inferior end 652 is disposed in laser probe proximal fixation mechanism housing 638. In one or more embodiments, laser probe proximal fixation mechanism 650 may be configured to fix piston tube housing 635 in handle base 645, e.g. laser probe proximal fixation mechanism 650 may comprise a setscrew configured to fix piston tube housing 635 in handle base 645.

Illustratively, piston tube 630 may be disposed in control mechanism 625, handle base 645, and laser probe nosecone 615. In one or more embodiments, a portion of laser probe nosecone 615 may be disposed in a portion of handle base 645, e.g., laser probe nosecone proximal end 617 may be disposed in handle base 645. Illustratively, threading 618 may be disposed in threading housing 685, e.g., threading 618 and threading housing 685 may be configured to fix a portion of laser probe nosecone 615 in a portion of handle base 645. In one or more embodiments, a portion of laser probe nosecone 615 may be fixed in a portion of handle base 645, e.g., a portion of laser probe nosecone 615 may be fixed in a portion of handle base 645 by an interference fit, an adhesive, a threading, a pin, a magnet, an epoxy, a weld, etc. Illustratively, piston tube 630 may be disposed in control mechanism 625 wherein piston tube distal end 631 is disposed in laser probe nosecone 615 and wherein piston tube proximal end 632 is disposed in piston tube housing 635. In one or more embodiments, piston tube 630 may be disposed in laser probe nosecone 615, housing tube sleeve guide 666, control mechanism guide 686, control mechanism 625, control mechanism inner bore 629, laser probe distal fixation mechanism chamber 670, piston tube housing receptacle 687, piston tube housing 635, and piston tube receptacle 680. Illustratively, piston tube 630 may be fixed in control mechanism 625, e.g., piston tube 630 may be fixed in control mechanism 625 by an interference fit, an adhesive, a threading, a pin, a magnet, an epoxy, a weld, etc. In one or more embodiments, piston tube 630 may be fixed in control mechanism 625 by laser probe distal fixation mechanism 620. Illustratively, laser probe distal fixation mechanism 620 may be disposed in control mechanism 625, e.g., laser probe distal fixation mechanism 620 may be disposed in laser probe distal fixation mechanism chamber 670. In one or more embodiments, laser probe distal fixation mechanism 620 may be disposed in control mechanism 625 wherein laser probe distal fixation mechanism 620 is configured to fix piston tube 630 in control mechanism 625, e.g., laser probe distal fixation mechanism 620 may comprise a setscrew configured to fix piston tube 630 in control mechanism 625.

Illustratively, control mechanism 625 may be disposed in control mechanism guide 686, e.g., control mechanism base 628 may be disposed in control mechanism guide 686 wherein control mechanism superior end 626 extends out from control mechanism guide 686. In one or more embodiments, control mechanism 625 may be configured to actuate within control mechanism guide 686, e.g., a user may actuate control mechanism 625 within control mechanism guide 686 by applying a force to a portion of control mechanism. Illustratively, an actuation of control mechanism 625 within control mechanism guide 686 may be configured to actuate piston tube 630 within handle base 645. Illustratively, an extension of control mechanism 625 relative to handle base proximal end 647 may be configured to extend piston tube 630 relative to handle base proxies mal end 647. In one or more embodiments, a retraction of control mechanism 625 relative to handle base proximal end 647 may be configured to retract piston tube 630 relative to handle base proximal end 647.

Illustratively, a portion of housing tube sleeve 610 may be disposed in piston tube 630, e.g., a portion of housing tube sleeve 610 may be disposed in piston tube inner lumen 675. In one or more embodiments, housing tube sleeve 610 may be disposed in housing tube sleeve guide 665, piston tube guide 666, control mechanism inner bore 629, piston tube 630, piston tube inner lumen 675, and piston tube receptacle 680. Illustratively, housing tube sleeve 610 may be disposed in piston tube inner lumen 675 wherein housing tube sleeve proximal end 612 is adjacent to piston tube proximal end 632. In one or more embodiments, housing tube sleeve 610 may be fixed in piston tube inner lumen 675, e.g., housing tube sleeve 610 may be fixed in piston tube inner lumen 675 by an interference fit, an adhesive, a threading, a pin, a magnet, an epoxy, a weld, etc. Illustratively, housing tube sleeve 610 may be fixed in piston tube 630 wherein an actuation of piston tube 630 is configured to actuate housing tube sleeve 610. In one or more embodiments, an extension of piston tube 630 relative to handle base proximal end 647 may be configured to extend housing tube sleeve 610 relative to handle base proximal end 647. Illustratively, a retraction of piston tube 630 relative to handle base proximal end 647 may be configured to retract housing tube sleeve 610 relative to handle base proximal end 647.

In one or more embodiments, housing tube 605 may be disposed in housing tube sleeve 610, e.g., housing tube 605 may be disposed in housing tube sleeve inner diameter 613. Illustratively, housing tube 605 may be disposed in housing tube sleeve 610, housing tube sleeve inner diameter 613, laser probe nosecone 615, housing tube sleeve guide 665, piston tube guide 666, piston tube 630, piston tube inner lumen 675, control mechanism 625, control mechanism inner bore 629, control mechanism inner chamber 670, piston tube housing 635, piston tube receptacle 680, housing tube guide 681, and optic fiber guide 682. In one or more embodiments, housing tube 605 may be disposed in piston tube housing 635 wherein a portion of housing tube 605 is fixed in piston tube housing 635, e.g., housing tube proximal end 605 may be fixed in piston tube housing 635. In one or more embodiments, a portion of housing tube 605 may be fixed in a portion of piston tube housing 635, e.g., a portion of housing tube 605 may be fixed in a portion of piston tube housing by an interference fit, an adhesive, a threading, a pin, a magnet, an epoxy, a weld, etc.

Illustratively, when control mechanism 625 is fully retracted in control mechanism guide 686, an assembled multi-component laser probe may comprise an assembled multi-component laser probe with a curved housing tube 700. In one or more embodiments, extending control mechanism 625 in control mechanism guide 686 may be configured to extend piston tube 630 relative to handle base proximal end 647. Illustratively, an extension of piston tube 630 relative to handle base proximal end 647 may be configured to extend housing tube sleeve 610 relative to handle base proximal end 647. In one or more embodiments, an extension of housing tube sleeve 610 relative to handle base proximal end 647 may be configured to extend housing tube sleeve 610 relative to housing tube 605. Illustratively, when control mechanism 625 is fully extended in control mechanism guide 686, an assembled multi-component laser probe may comprise an assembled multi-component laser probe with a straightened housing tube 800.

In one or more embodiments, connector distal housing 689, connector medial housing 690, and connector proximal housing 691 may have a functionality of housing a connector, e.g., connector distal housing 689, connector medial housing 690, and connector proximal housing 691 may have a functionality of housing an optic fiber connects or. Illustratively, connector distal housing 689, connector medial housing 690, and connector proximal housing 691 may have a functionality of temporarily housing an optic fiber connector wherein a distal end of an optic fiber of the optic fiber connector is disposed adjacent to housing tube distal end 606, e.g., connector distal housing 689, connector medial housing 690, and connector proximal housing 691 may have a functionality of temporarily housing an optic fiber connector wherein a distal end of an optic fiber of the optic fiber connector is disposed coplanar with housing tube distal end 606. In one or more embodiments, proximal taper 683 may have a functionality of guiding a distal end of an optic fiber of an optic fiber connector into optic fiber guide 682, e.g., proximal taper 683 may have a functionality of funneling a distal end of an optic fiber of an optic fiber connector into optic fiber guide 682. Illustratively, optic fiber guide 682 may have a functionality of fixing housing tube 605 in a position relative to housing tube sleeve 610, e.g., optic fiber guide 682 may have a functionality of fixing housing tube 605 in a position relative to piston tube 630. In one or more embodiments, piston tube housing receptacle 687 may have a functionality of housing piston tube housing 635, e.g., piston tube housing receptacle 687 may have a functionality of aligning piston tube housing 635 wherein piston tube receptacle 680 is collinear with piston tube 630. Illustratively, piston tube receptacle 680 may have a functionality of aligning piston tube 630 within handle base 645, e.g., piston tube receptacle 680 may have a functionality of limiting an amount of actuation of piston tube 630 towards handle base proximal end 647 and away from handle base distal end 646. In one or more embodiments, piston tube receptacle 680 may have a functionality of aligning piston tube 630 wherein piston tube 630 is collinear with piston tube guide 666, e.g., piston tube receptacle 680 may have a functionality of aligning piston tube inner lumen 675 wherein piston tube inner lumen 675 is collinear with housing tube guide 681. Illustratively, laser probe proximal fixation mechanism 650 may have a functionality of fixing piston tube housing 635 in piston tube housing receptacle 687. In one or more embodiments, piston tube 630 may have a functionality of housing housing tube sleeve 610, e.g., piston tube inner lumen 675 may have a functionality of housing housing tube sleeve 610. Illustratively, piston tube 630 may have a functionality of actuating housing tube sleeve 610 relative to housing tube 605. In one or more embodiments, piston tube inner lumen 675 may have a functionality of fixing housing tube sleeve 610 in piston tube 630, e.g., piston tube inner lumen 675 may have a functionality of aligning housing tube sleeve 610 within handle base 645 wherein housing tube sleeve 610 is collinear with housing tube sleeve guide 665. Illustratively, control mechanism inner bore 629 may have a functionality of housing piston tube 630, e.g., control mechanism inner bore 629 may have a functionality of fixing piston tube 630 in control mechanism 625. In one or more embodiments, laser probe distal fixation mechanism 620 may have a functionality of fixing piston tube 630 in control mechanism 625, e.g., laser probe distal fixation mechanism 620 may have a functionality of fixing control mechanism 625 to piston tube 630. Illustratively, laser probe distal fixation mechanism 620 and piston tube 630 may have a functionality of fixing control mechanism 625 in control mechanism guide 686, e.g., a length of piston tube 630 and a distance between piston tube housing distal end 636 and laser probe nosecone proximal end 617 may be configured to fix piston tube 630 in piston tube receptacle 680 and piston tube guide 666 and laser probe distal fixation mechanism 620 may be configured to fix control mechanism 625 to piston tube 630. In one or more embodiments, control mechanism guide 686 may have a functionality of limiting an amount of actuation of control mechanism 625 towards laser probe nosecone 615 and away from handle base proximal end 647, e.g., control mechanism guide 686 may have a functionality of limiting an amount of actuation of control mechanism 625 towards handle base proximal end 647 and away from laser probe nosecone 615. Illustratively, control mechanism 625 may have a functionality of housing piston tube 630, e.g., control mechanism 625 may have a functionality of actuating piston tube 630 relative to housing tube 605. In one or more embodiments, control mechanism 625 may have a functionality of actuating housing tube sleeve 610 relative to housing tube 605, e.g., control mechanism 625 may have a functionality of adjusting an amount of curvature of housing tube 605. Illustratively, piston tube guide 666 may have a functionality of housing piston tube 630, e.g., piston tube guide 666 may have a functionality of aligning piston tube 630 wherein piston tube 630 is collinear with piston tube receptacle 680.

FIGS. 9A and 9B are schematic diagrams illustrating an exploded view of a single-component laser probe assembly 900. FIG. 9A illustrates a side view of a singles component laser probe assembly 900. FIG. 9B illustrates a cross-sectional view in a sagittal plane of a single-component laser probe assembly 900. Illustratively, a single-component laser probe assembly 900 may comprise a housing tube 605, a housing tube sleeve 610, and an integral handle base 945. In one or more embodiments, housing tube 605 may comprise a housing tube distal end 606 and a housing tube proximal end 607. Illustratively, housing tube 605 may comprise a housing tube inner diameter 608. In one or more embodiments, housing tube sleeve 610 may comprise a housing tube sleeve distal end 611 and a housing tube sleeve proximal end 612. Illustratively, housing tube sleeve 610 may comprise a housing tube sleeve inner diameter 613. In one or more embodiments, integral handle base 945 may comprise an integral handle base distal end 946 and an integral handle base proximal end 947. Illustratively, integral handle base 945 may comprise a control mechanism anchor 901. In one or more embodiments, control mechanism anchor 901 may comprise a first side 902 and a second side 903. Illustratively, integral handle base 945 may comprise a control mechanism anchor guide 905. In one or more embodiments, control mechanism anchor guide 905 may comprise a control mechanism anchor guide distal end 906 and a control mechanism anchor guide proximal end 907. Illustratively, integral handle base 945 may comprise a control mechanism restraint 910. In one or more embodiments, integral handle base 945 may comprise an integral laser probe nosecone 915. Illustratively, integral handle base 945 may comprise an integral control mechanism 925. In one or more embodiments, integral control mechanism 925 may comprise an integral control mechanism superior end 926 and an integral control mechanism base 928. Illustratively, integral handle base 945 may comprise an integral piston tube 930. In one or more embodiments, integral piston tube 930 may comprise an integral piston tube distal end 931 and an integral piston tube proximal end 932. Illustratively, integral handle base 945 may comprise an integral laser probe identification ring 960. In one or more embodiments, integral handle base 945 may comprise an integral housing tube sleeve guide 965. Illustratively, integral handle base 945 may comprise an integral piston tube guide 966. In one or more embodiments, integral handle base 945 may comprise an integral piston tube inner lumen 975. Illustratively, integral handle base 945 may comprise an integral housing tube guide 981. In one or more embodiments, integral handle base 945 may comprise an integral optic fiber guide 982. Illustratively, integral handle base 945 may comprise an integral proximal taper 983. In one or more embodiments, integral handle base 945 may comprise an integral control mechanism guide 986. Illustratively, integral handle base 945 may comprise an integral connector housing 989. In one or more embodiments, integral handle base 945 a distal residual material vent 992. Illustratively, integral handle base 945 may comprise a medico al residual material vent 993. In one or more embodiments, integral handle base 945 may comprise one or more proximal residual material vents 994. Illustratively, integral handle base 945 may comprise an integral housing tube guide access lumen 997.

Illustratively, one or more portions of integral handle base 945 may be manufactured by additive manufacturing, e.g., one or more portions of integral handle base 945 may be manufactured by selective laser sintering, selective heat sintering, selective laser melting, electron-beam melting, direct metal laser sintering, electron beam freeform fabrication, stereolithography, digital light processing, fused deposition modeling, laminated object manufacturing, ultrasonic additive manufacturing, vat photopolymerization, material jetting, binder jetting, laser engineered net shaping, etc. In one or more embodiments, integral handle base 945 may be manufactured entirely by additive manufacturing, e.g., integral handle base 945 may be manufactured entirely by selective laser sintering, selective heat sintering, selective laser melting, electron-beam melting, direct metal laser sintering, electron beam freeform fabrication, stereolithography, digital light processing, fused deposition modeling, laminated object manufacturing, ultrasonic additive manufacturing, vat photopolymerization, material jetting, binder jetting, laser engineered net shaping, etc. For example, integral handle base 945 may be manufactured by selective laser sintering from a nylon material.

Figure 11A:
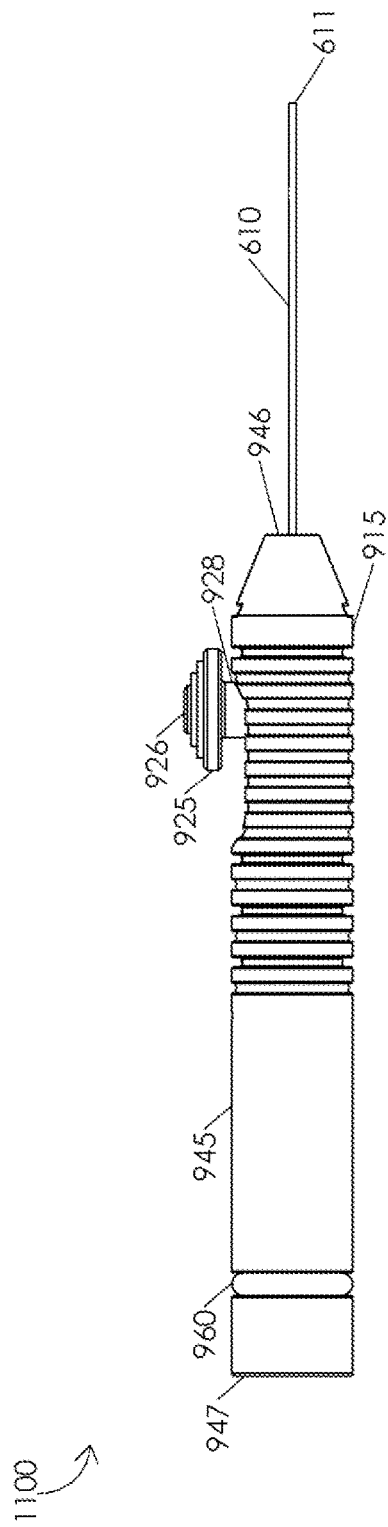
Figure 11B:
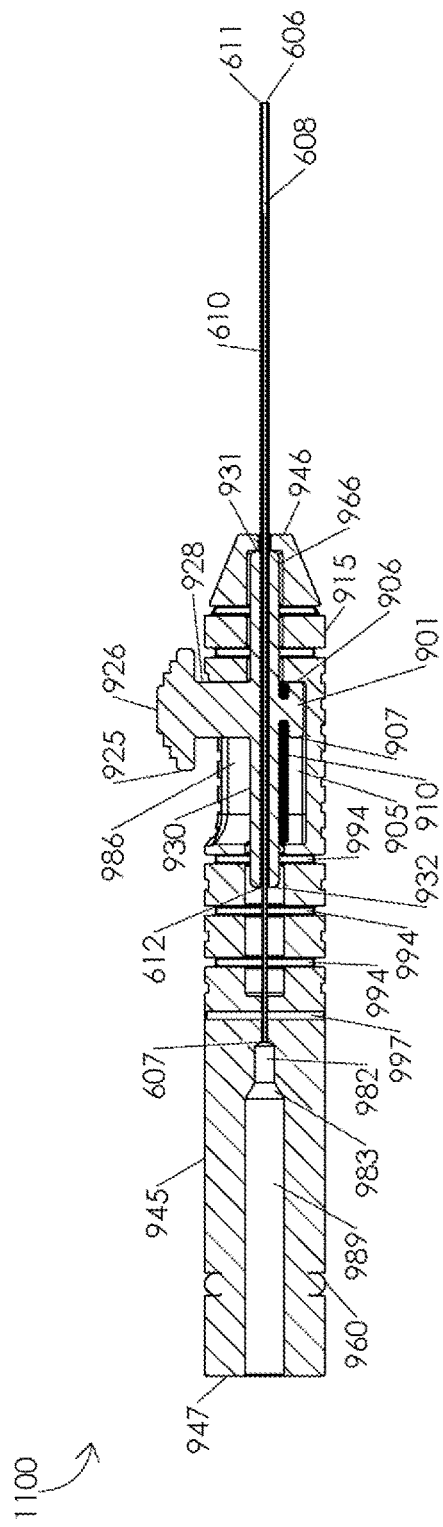

FIGS. 10A, 10B, 11A, 11B, 12A, and 12B are schematic diagrams illustrating an assembled single-component laser probe. FIG. 10A illustrates a side view of an assembled single-component laser probe with a curved housing tube 1000. FIG. 10B illustrates a cross-sectional view in a sagittal plane of an assembled single-component laser probe with a curved housing tube 1000. FIG. 11A illustrates a side view of an assembled single-component laser probe with a straightened housing tube 1100. FIG. 11B illustrates a cross-sectional view in a sagittal plane of an assembled single-component laser probe with a straightened housing tube 1100. FIG. 12A illustrates a superior view of an assembled single-component laser probe with a curved housing tube 1200. FIG. 12B illustrates a cross-sectional view in a frontal plane of an assembled single-component laser probe with a curved housing tube 1201. Illustratively, control mechanism anchor 901 may be disposed in control mechanism anchor guide 905, e.g., control mechanism anchor first side 902 and control mechanism anchor second side 903 may be disposed in control mechanism anchor guide 905. In one or more embodiments, integral control mechanism base 928 may be disposed in integral control mechanism guide 986. Illustratively, control mechanism restraint 910 may be disposed between control mechanism anchor guide 905 and control mechanism guide 986, e.g., control mechanism restraint 910 may be disposed between control mechanism anchor 901 and integral control mechanism base 928. In one or more embodiments, an actuation of integral control mechanism 925 in integral control mechanism guide 986 may be configured to actuate control mechanism anchor 901 in control mechanism anchor guide 905. Illustratively, an extension of integral control mechanism 925 relative to integral handle base proximal end 947 may be configured to extend control mechanism anchor 901 relative to integral handle base proximal end 947. In one or more embodiments, a retraction of integral control mechanism 925 relative to integral handle base proximal end 947 may be configured to retract control mechanism anchor 901 relative to integral handle base proximal end 947.

Illustratively, one or more proximal residual material vents 994 may be configured to remove free particles of material disposed around integral piston tube 930 as a result of an additive manufacturing process, e.g., a high-pressure gas may be forced to flow through one or more proximal residual material vents 994 to remove free particles of material disposed around integral piston tube 930 as a result of an additive manufacturing process. In one or more embodiments, one or more medial residual material vents 993 may be configured to remove free particles of material disposed around integral piston tube 930 as a result of an additive manufacturing process, e.g., a high-pressure gas may be forced to flow through one or more medial residual material vents 993 to remove free particles of material disposed around integral piston tube 930 as a result of an additive manufacturing process. Illustratively, one or more distal residual material vents 992 may be configured to remove free particles of material disposed around integral piston tube 930 as a result of an additive manufacturing process, e.g., a high-pressure gas may be forced to flow through one or more distal residual material vents 992 to remove free particles of material disposed around integral piston tube 930 as a result of an additive manufacturing process.

Illustratively, housing tube sleeve 610 may be disposed in integral housing tube sleeve guide 965, integral piston tube guide 966, integral control mechanism guide 986, integral control mechanism 925, integral piston tube 930, and integral piston tube inner lumen 975. In one or more embodiments, housing tube sleeve 610 may be disposed in integral piston tube inner lumen 975 wherein housing tube proximal end 912 is adjacent integral piston tube proximal end 932. Illustratively, housing tube sleeve 610 may be fixed integral piston tube 930, e.g., housing tube sleeve 610 may be fixed in integral piston tube 930 by an interference fit, an adhesive, a threading, a pin, a magnet, an epoxy, a weld, etc. In one or more embodiments, housing tube sleeve 610 may be fixed in integral piston tube 930 wherein an actuation of piston tube 930 may be configured to actuate housing tube sleeve 610. Illustratively, an actuation of integral control mechanism 925 may be configured to actuate integral piston tube 930. In one or more embodiments, an extension of integral control mechanism 925 relative to integral handle base proximal end 947 may be configured to extend integral piston tube 930 relative to integral handle base proximal end 947. Illustratively, a retraction of integral control mechanism 925 relative to integral handle base proximal end 947 may be configured to retract integral piston tube 930 relative to integral handle base proximal end 947. In one or more embodiments, an extension of integral piston tube 930 relative to integral handle base proximal end 947 may be configured to extend housing tube sleeve 610 relative to integral handle base proximal end 947. Illustratively, a retraction of integral piston tube 930 relative to integral handle base proximal end 947 may be configured to retract housing tube sleeve 610 relative to integral handle proximal end 947.

In one or more embodiments, housing tube 605 may be disposed in housing tube sleeve 610, e.g., housing tube 605 may be disposed in housing tube sleeve inner diameter 613. Illustratively, housing tube 605 may be disposed in housing tube sleeve 610, housing tube sleeve inner diameter 613, integral housing tube sleeve guide 965, integral piston tube guide 966, integral control mechanism guide 986, integral control mechanism 925, integral piston tube 930, integral piston tube inner lumen 975, and integral housing tube housing 981. In one or more embodiments, a portion of housing tube 605 may be fixed in integral housing tube housing 981, e.g., a portion of housing tube 605 may be fixed in integral housing tube housing 981 by an interference fit, an adhesive, a threading, a pin, a magnet, an epoxy, a weld, etc. Illustratively, an extension of integral control mechanism 925 in integral control mechanism guide 986 may be configured to extend integral piston tube 930 relative to housing tube 605. In one or more embodiments, an extension of integral piston tube 930 relative to housing tube 605 may be configured to extend housing tube sleeve 610 relative to housing tube 605. Illustratively, a retraction of integral control mechanism 925 in integral control mechanism guide 986 may be configured to retract integral piston tube 930 relative to housing tube 605. In one or more embodiments, a retraction of integral piston tube 930 relative to housing tube 605 may be configured to retract housing tube sleeve 610 relative to housing tube 605. Illustratively, when integral control mechanism 925 is fully retracted in integral control mechanism guide 986, an assembled single-component laser probe may comprise an assembled single-component laser probe with a curved housing tube 1000. In one or more embodiments, when integral control mechanism 925 is fully extended in integral control mechanism guide 986, an assembled single-component laser probe may comprise an assembled single-component laser probe with a straightened housing tube 1100.

Illustratively, integral laser probe identification ring 960 may be configured to indicate one or more properties of an assembled single-component laser probe to a user or a surgeon, e.g., integral laser probe identification ring 960 may be configured to indicate a type or size of cannula that is compatible with an assembled single-component laser probe. In one or more embodiments, control mechanism anchor 901 may have a functionality of fixing integral control mechanism 925 in integral control mechanism guide 986, e.g., control mechanism restraint 910 may have a functionality of fixing integral control mechanism 925 in integral control mechanism guide 986. Illustratively, integral nosecone 915 may have a functionality of housing a portion of integral piston tube 930, e.g., integral piston tube guide 966 may have a functionality of housing a portion of integral piston tube 930. In one or more embodiments, integral nosecone 915 may have a functionality of aligning housing tube sleeve 610, e.g., integral housing tube sleeve guide 965 may have a functionality of aligning housing tube sleeve 610. Illustratively, integral control mechanism 925 may have a functionality of actuating integral piston tube 930, e.g., integral control mechanism 925 may have a functionality of actuating integral piston tube 930 relative to housing tube 605. In one or more embodiments, integral piston tube 930 may have a functionality of housing housing tube sleeve 610, e.g., integral piston tube inner lumen 975 may have a functionality of housing housing tube sleeve 610. Illustratively, integral housing tube housing 981 may have a functionality of fixing housing tube 605 in a position relative to housing tube sleeve 610, e.g., integral housing tube housing 981 may have a functionality of fixing housing tube 605 in a position relative to integral piston tube 930. In one or more embodiments, integral proximal taper 983 may have a functionality of guiding a distal end of an optic fiber of an optic fiber connector into integral optic fiber guide 982, e.g., integral proximal taper 983 may have a functionality of funneling a distal end of an optic fiber of an optic fiber connector into integral optic fiber guide 982. Illustratively, integral connector housing 989 may have a functionality of temporarily housing an optic fiber connector wherein a distal end of an optic fiber of the optic fiber connector is disposed adjacent to housing tube distal end 606, e.g., integral connector housing 989 may have a functionality of temporarily housing an optic fiber connector wherein a distal end of an optic fiber of the optic fiber connector is disposed coplanar with housing tube distal end 606.

In one or more embodiments, integral handle base 945 may be manufactured by additive manufacturing wherein one or more subcomponents of a multi-component laser probe assembly 600 are eliminated but a functionality of the one or more subcomponents is retained, e.g., integral laser probe nosecone 915 eliminates laser probe nosecone 615 as a subcomponent but retains a functionality of housing integral piston tube 930. Illustratively, integral handle base 945 may be manufactured by additive manufacturing wherein laser probe proximal fixation mechanism 650 and piston tube housing 635 are eliminated as subcomponents of a multi-component laser probe assembly 600 but a functionality of housing integral piston tube 930 is retained. Illustratively, integral laser probe identification ring 960 may be manufactured by additive manufacturing wherein one or more subcomponents of a multi-component laser probe assembly 600 are eliminated but a functionality of the one or more subcomponents is retained, e.g., integral laser probe identification ring 960 eliminates laser probe identification ring 660 as a subcomponent but retains a functionality of indicating one or more properties of an assembled single-component laser probe to a user or a surgeon. In one or more embodiments, integral control mechanism 925 may be manufactured by additive manufacturing wherein one or more subcomponents of a multi-component laser probe assembly 600 are eliminated but a functionality of the one or more subcomponents is retained, e.g., integral control mechanism 925 eliminates control mechanism 625 as a subcomponent but retains a functionality of actuating integral piston tube 930. Illustratively, control mechanism anchor 901 may be manufactured by additive manufacturing wherein one or more subcomponents of a multi-component laser probe assembly 600 are eliminated but a functionality of the one or more subcomponents is retained, e.g., control mechanism anchor 901 eliminates laser probe distal fixation mechanism 620 and piston tube 630 as subcomponents but retains a functionality of fixing integral control mechanism 925 in integral control mechanism guide 986. In one or more embodiments, control mechanism restraint 910 may be manufactured by additive manufacturing wherein one or more subcomponents of a multi-component laser probe assembly 600 are eliminated but a functionality of the one or more subcomponents is retained, e.g., control mechanism restraint 910 eliminates laser probe distal fixation mechanism 620 as a subcomponent but retains a functionality of fixing integral control mechanism 925 in integral control mechanism guide 986. Illustratively, integral piston tube 930 may be manufactured by additive manufacturing wherein one or more subcomponents of a multi-component laser probe assembly 600 are eliminated but a functionality of the one or more subcomponents is retained, e.g., integral piston tube 930 eliminates piston tube 630 as a subcomponent but retains a functionality of actuating housing tube sleeve 610 relative to housing tube 605.

In one or more embodiments, an assembled single-component laser probe may comprise one or more elements configured to facilitate manufacturing integral handle base 945 by additive manufacturing, e.g., one or more distal residual material vents 992 may be configured to facilitate manufacturing integral handle base 945 by additive manufacturing. Illustratively, one or more medial residual material vents 993 may be configured to facilitate manufacturing integral handle base 945 by additive manufacturing. In one or more embodiments, one or more proximal residual material vents 994 may be configured to facilitate manufacturing integral handle base 945 by additive manufacturing. Illustratively, integral housing tube guide access lumen 997 may be configured to facilitate manufacturing integral handle base 945 by additive manufacturing.

FIGS. 13A and 13B are schematic diagrams illustrating an exploded view of a multi-component scleral depressor assembly 1300. FIG. 13A illustrates a side view of a multi-component scleral depressor assembly 1300. FIG. 13B illustrates a cross-sectional view in a sagittal plane of a multi-component scleral depressor assembly 1300. In one or more embodiments, a multi-component scleral depressor assembly 1300 may comprise an upper container 1305, a lower container 1310, an actuation platform 1315, a compression spring 1320, a pin 1325, a lever 1330, a lever control 1340, a depressor 1345, and a depressor fixation mechanism 1350. Illustratively, upper container 1305 may comprise an upper container superior end 1306 and an upper container inferior end 1307. In one or more embodiments, upper container 1305 may comprise a compression spring interface 1309. Illustratively, upper container 1305 may comprise a lever guide 1318. In one or more embodiments, upper container 1305 may comprise a superior concavity 1356. Illustratively, upper container 1305 may be manufactured from any suitable material, e.g., polymers, metals, metal alloys, etc., or from any combination of suitable materials. For example, upper container 1305 may be manufactured by a machining process, a casting process, a molding process, a forming process, a coating process, a joining process, etc. In one or more embodiments, lower container 1310 may comprise a lower container superior end 1311 and a lower container inferior end 1312. Illustratively, lower container 1310 may comprise an upper container interface 1313. In one or more embodiments, lower container 1310 may comprise a pin housing 1314. Illustratively, lower container 1310 may comprise an inferior actuation platform housing 1303. In one or more embodiments, lower container 1310 may comprise an actuation platform interface 1304. Illustratively, lower container 1310 may comprise an inferior concavity 1355. In one or more embodiments, lower container 1310 may be manufactured from any suitable material, e.g., polymers, metals, metal alloys, etc., or from any combination of suitable materials. For example, lower container 1310 may be manufactured by a machining process, a casting process, a molding process, a forming process, a coating process, a joining process, etc. Illustratively, actuation platform 1315 may comprise a pin guide 1316. In one or more embodiments, actuation platform 1315 may comprise a compression spring housing 1317. Illustratively, actuation platform 1315 may comprise a lever housing 1319. In one or more embodiments, actuation platform 1315 may be manufactured from any suitable material, e.g., polymers, metals, metal alloys, etc., or from any combination of suitable materials. For example, actuation platform 1315 may be manufactured by a machining process, a casting process, a molding process, a forming process, a coating process, a joining process, etc. Illustratively, compression spring 1320 may be manufactured from any suitable material, e.g., polymers, metals, metal alloys, etc., or from any combination of suitable materials. For example, compression spring 1320 may be manufactured by a machining process, a casting process, a molding process, a forming process, a coating process, a joining process, etc. In one or more embodiments, pin 1325 may be manufactured from any suitable material, e.g., polymers, metals, metal alloys, etc., or from any combination of suitable materials. For example, pin 1325 may be manufactured by a machining process, a casting process, a molding process, a forming process, a coating process, a joining process, etc. Illustratively, lever 1330 may comprise a lever distal end 1331 and a lever proximal end 1332. In one or more embodiments, lever 1330 may comprise a lever housing interface 1333. Illustratively, lever 1330 may comprise lever control housing 1334. In one or more embodiments, lever 1330 may comprise a depressor fixation mechanism proximal housing 1335. For example, lever 1330 may comprise a lever outer diameter 1360. Illustratively, lever 1330 may be manufactured from any suitable material, e.g., polymers, metals, metal alloys, etc., or from any combination of suitable materials. For example, lever 1330 may be manufactured by a machining process, a casting process, a molding process, a forming process, a coating process, a joining process, etc. In one or more embodiments, lever control 1340 may comprise a lever control inferior end 1341 and a lever control superior end 1342. Illustratively, lever control 1340 may comprise a lever control housing interface 1343. In one or more embodiments, lever control 1340 may be manufactured from any suitable material, e.g., polymers, metals, metal alloys, etc., or from any combination of suitable materials. For example, lever control 1340 may be manufactured by a machining process, a casting process, a molding process, a forming process, a coating process, a joining process, etc. Illustratively, depressor 1345 may comprise a depressor fixation mechanism medial housing 1346. In one or more embodiments, depressor 1345 may comprise a depressor fixation mechanism distal housing 1347. Illustratively, depressor 1345 may be manufactured from any suitable material, e.g., polymers, metals, metal alloys, etc., or from any combination of suitable materials. For example, depressor 1345 may be manufactured by a machining process, a casting process, a molding process, a forming process, a coating process, a joining process, etc. In one or more embodiments, depressor fixation mechanism 1350 may comprise a depressor fixation mechanism distal end 1351 and a depressor fixation mechanism proximal end 1352. Illustratively, depressor fixation mechanism 1350 may be manufactured from any suitable material, e.g., polymers, metals, metal alloys, etc., or from any combination of suitable materials. For example, depressor fixation mechanism 1350 may be manufactured by a machining process, a casting process, a molding process, a forming process, a coating process, a joining process, etc.

FIGS. 14A, 14B, 15A, 15B, 16A, and 16B are schematic diagrams illustrating an assembled multi-component scleral depressor. FIG. 14A illustrates a side view of an assembled multi-component scleral depressor with an actuated lever 1400. FIG. 14B illustrates a cross-sectional view in a sagittal plane of an assembled multi-component scleral depressor with an actuated lever 1400. FIG. 15A illustrates a superior view of an assembled multi-component scleral depressor with an actuated lever 1500. FIG. 15B illustrates a cross-sectional view in a frontal plane of an assembled multi-component scleral depressor with an actuated lever 1501. FIG. 16A illustrates a side view of an assembled multi-component scleral depressor with an unactuated lever 1600. FIG. 16B illustrates a cross-sectional view in a sagittal plane of an assembled multi-component scleral depressor with an unactuated lever 1600.

Illustratively, a portion of lower container 1310 may be disposed in a portion of upper container 1305, e.g., lower container superior end 1311 may be disposed in a portion of upper container 1305. In one or more embodiments, a portion of lower container 1310 may be disposed in a portion of upper container 1305 wherein upper container inferior end 1307 is adjacent to upper container interface 1313, e.g., a portion of lower container 1310 may be disposed in a portion of upper container 1305 wherein upper container inferior end 1307 abuts upper container interface 1313. Illustratively, a portion of lower container 1310 may be fixed in a portion of upper container 1305, e.g., a portion of lower container 1310 may be fixed in a portion of upper container 1305 by an interference fit, an adhesive, a threading, a pin, a magnet, an epoxy, a weld, etc. In one or more embodiments, actuation platform 1315 may be disposed in lower container 1310 and upper container 1305, e.g., actuation platform 1315 may be disposed in inferior actuation platform housing 1303. Illustratively, actuation platform 1315 may be disposed in lower container 1310 and upper container 1305 wherein actuation platform 1315 is disposed between upper container superior end 1306 and lower container inferior end 1312. In one or more embodiments, actuation platform 1315 may be disposed in lower container 1310 and upper container 1305 wherein actuation platform 1315 is disposed between inferior concavity 1355 and superior concavity 1356. Illustratively, actuation platform 1315 may be disposed in lower container 1310 and upper container 1305 wherein pin guide 1316 is aligned with pin housing 1314, e.g., actuation platform 1315 may be disposed in lower container 1310 and upper container 1305 wherein pin guide 1316 and pin housing 1314 are collinear. In one or more embodiments, actuation platform 1315 may be fixed in lower container 1310 and upper container 1305, e.g., actuation platform 1315 may be fixed in lower container 1310 and upper container 1305 by an interference fit, an adhesive, a threading, a pin, a magnet, an epoxy, a weld, etc. Illustratively, actuation platform 1315 may be fixed in lower container 1310 and upper container 1305 by pin 1325, e.g., pin 1325 may be disposed in pin housing 1314 and pin guide 1316. In one or more embodiments, pin 1325 may be fixed in pin housing 1314, e.g., pin 1325 may be fixed in pin housing 1314 by an interference fit, an adhesive, a threading, a pin, a magnet, an epoxy, a weld, etc. Illustratively, actuation platform 1315 may be configured to actuate about pin 1325 in lower container 1310 and upper container 1305, e.g., actuation platform 1315 may be configured to rotate about pin 1325 in lower container 1310 and upper container 1305 in a first direction and a second direction.

In one or more embodiments, compression spring 1320 may be disposed in a portion of upper container 1305, a portion of lower container 1310, and a portion of actuation platform 1315, e.g., compression spring 1320 may be disposed in a portion of upper container 1305, a portion of lower container 1310, and a portion of actuation platform 1315 wherein a portion of compression spring 1320 is disposed in compression spring housing 1317. Illustratively, compression spring 1320 may be disposed in a portion of upper container 1305, a portion of lower container 1310, and a portion of actuation plats form 1315 wherein a first end of compression spring 1320 is adjacent to compression spring interface 1309 and a second end of compression spring 1320 is disposed in compression spring housing 1317, e.g., compression spring 1320 may be disposed in a portion of upper container 1305, a portion of lower container 1310, and a portion of actuation platform 1315 wherein a first end of compression spring 1320 abuts compression spring interface 1309 and a second end of compression spring 1320 is disposed in compression spring housing 1317. In one or more embodiments, a portion of compression spring 1320 may be fixed in compression spring housing 1317, e.g., a portion of compression spring 1320 may be fixed in compression spring housing 1317 by an interference fit, an adhesive, a threading, a pin, a magnet, an epoxy, a weld, etc. Illustratively, compression spring 1320 may be configured to provide a force, e.g., compression spring 1320 may be configured to apply a force to a portion of actuation platform 1315. In one or more embodiments, compression spring 1320 may be configured to apply a force to a portion of actuation platform 1315 wherein the force resists a rotation of actuation platform 1315 about pin 1325 in a first direction. Illustratively, compression spring 1320 may be configured to apply a force to a portion of actuation platform 1315 wherein the force facilitates a rotation of actuation platform 1315 about pin 1325 in a second direction.

In one or more embodiments, a portion of lever 1330 may be disposed in a portion of actuation platform 1315, e.g., lever housing interface 1333 may be disposed in lever housing 1319. Illustratively, a portion of lever 1330 may be fixed in a portion of actuation platform 1315, e.g., a portion of lever 1330 may be fixed in a portion of actuation platform 1315 by an interference fit, an adhesive, a threading, a pin, a magnet, an epoxy, a weld, etc. In one or more embodiments, a portion of lever 1330 may be disposed in a portion of upper container 1305, a portion of lower container 1310, a portion of actuation platform 1315, and lever guide 1318. Illustratively, lever 1330 may be configured to actuate within lever guide 1318. In one or more embodiments, a portion of lever control 1340 may be disposed in a portion of lever 1330, e.g., lever control housing interface 1343 may be disposed in lever control housing 1334. Illustratively, a portion of lever control 1340 may be fixed in a portion of lever 1330, e.g., a portion of lever control 1340 may be fixed in a portion of lever 1330 by an interference fit, an adhesive, a threading, a pin, a magnet, an epoxy, a weld, etc. In one or more embodiments, a portion of lever control 1340 may be disposed in a portion of lever 1330 wherein a portion of lever control 1340 extends out from lever 1330, e.g., lever control inferior end 1341 may be disposed in a portion of lever 1330 and lever control superior end 1342 may extend out from lever 1330.

Illustratively, depressor 1345 may be fixed to a portion of lever 1330, e.g., depressor 1345 may be fixed to lever distal end 1331. In one or more embodiments, depressor 1345 may be fixed to a portion of lever 1330 by an interference fit, an adhesive, a threading, a pin, a magnet, an epoxy, a weld, etc. Illustratively, depressor fixation mechanism 1350 may be configured to fix depressor 1345 to a portion of lever 1330, e.g., depressor fixation mechanism 1350 may be configured to fix depressor 1345 to lever distal end 1331. In one or more embodiments, depressor fixation mechanism 1350 may be disposed in a portion of depressor 1345 and disposed in a portion of lever 1330, e.g., depressor fixation mechanism 1350 may be disposed in depressor fixation mechanism proximal housing 1335, depressor fixation mechanism medial housing 1346, and depressor fixation mechanism distal housing 1347. Illustratively, depressor fixation mechanism 1350 may be fixed in depressor fixation mechanism proximal housing 1335, depressor fixation mechanism medial housing 1346, and depressor fixation mechanism distal housing 1347, e.g., depressor fixation mechanism 1350 may be fixed in depressor fixation mechanism proximal housing 1335, depressor fixation mechanism medial housing 1346, and depressor fixation mechanism distal housing 1347 by an interference fit, an adhesive, a threading, a pin, a magnet, an epoxy, a weld, etc.

In one or more embodiments, a user may apply a force to lever control 1340 of assembled multi-component scleral depressor with an unactuated lever 1600, e.g., a user may apply a force to a portion of lever 1330 of assembled multi-component scleral depressor with an unactuated lever 1600. Illustratively, an application of a force to lever 1330 of assembled multi-component scleral depressor with an unactuated lever 1600 may be configured to actuate lever 1330 within lever guide 1318. In one or more embodiments, an actuation of lever 1330 within lever guide 1318 may be configured to rotate actuation platform 1315 about pin 1325, e.g., an actuation of lever 1330 within lever guide 1318 may be configured to rotate actuation platform 1315 about pin 1325 in a first direction. Illustratively, compression spring 1320 may be configured to apply a force to a portion of actuation platform 1315 configured to resist a rotation of actuation platform 1315 about pin 1325 in a first direction. In one or more embodiments, an actuation of actuation platform 1315 in a first direction may be configured to depress a patient's sclera, e.g., depressor 1345 may be configured to apply a force to a patient's sclera causing the patient's sclera to deform. Illustratively, an assembled multi-component scleral depressor may comprise an assembled multi-component scleral depressor with an actuated lever 1400 when a patient's sclera is depressed.

In one or more embodiments, a user may reduce or remove a force applied to lever control 1340 of assembled multi-component scleral depressor with an actuated lever 1400, e.g., a user may reduce or remove a force applied to a portion of lever 1330 of assembled multi-component scleral depressor with an actuated lever 1400. Illustratively, a reduction or a removal of a force applied to lever 1330 of assembled multi-component scleral depressor with an actuated lever 1400 may be configured to actuate lever 1330 within lever guide 1318. In one or more embodiments, an actuation of lever 1330 within lever guide 1318 may be configured to rotate actuation platform 1315 about pin 1325, e.g., an actuation of lever 1330 within lever guide 1318 may be configured to rotate actuation platform 1315 about pin 1325 in a second direction. Illustratively, compression spring 1320 may be configured to apply a force to a portion of actuation platform 1315 configured to facilitate a rotation of actuation platform 1315 about pin 1325 in a second direction. In one or more embodiments, an actuation of actuation platform 1315 in a second direction may be configured to raise a patient's sclera, e.g., depressor 1345 may be configured to reduce or remove a force applied to a patient's sclera causing the patient's sclera to deform. Illustratively, an assembled multi-component scleral depressor may comprise an assembled multi-component scleral depressor with an unactuated lever 1600 when a patient's sclera is raised.

In one or more embodiments, upper container 1305 may have a functionality of housing a portion of actuation platform 1315, e.g., upper container 1305 may have a functionality of housing a superior portion of actuation platform 1315. Illustratively, upper container 1305 may have a functionality of housing a portion of compression spring 1320, e.g., upper container 1305 may have a functionality of housing a superior portion of compression spring 1320. In one or more embodiments, lower container 1310 may have a functionality of housing a portion of actuation platform 1315, e.g., lower container 1310 may have a functionality of housing an inferior portion of actuation platform 1315. Illustratively, lower container 1310 may have a functionality of housing a portion of compression spring 1320, e.g., lower container 1310 may have a functionality of housing an inferior portion of compression spring 1320. In one or more embodiments, lower container 1310 may have a functionality of housing pin 1325. Illustratively, lower container 1310 may have a functionality of limiting an amount of actuation of actuation platform 1315 about pin 1325, e.g., lower container 1310 may have a functionality of limiting an amount of rotation of actuation platform 1315 about pin 1325 in a second direction. In one or more embodiments, actuation platform 1315 may have a functionality of counterbalancing lever 1330. Illustratively, actuation platform 1315 may have a functionality of housing a portion of compression spring 1320. In one or more embodiments, actuation platform 1315 may have a functionality of housing a portion of lever 1330. Illustratively, compression spring 1320 may have a functionality of providing a force. In one or more embodiments, compression spring 1320 may have a functionality of applying a force to a portion of actuation platform 1315 configured to resist a rotation of actuation platform 1315 about pin 1325 in a first direction. Illustratively, compression spring 1320 may have a functionality of applying a force to a portion of actuation platform 1315 configured to facilitate a rotation of actuation platform 1315 about pin 1325 in a second direction. In one or more embodiments, lever control 1340 may have a functionality of facilitating an actuation of lever 1330. Illustratively, lever 1330 may have a functionality of extending depressor 1345 from actuation platform 1315. In one or more embodiments, depressor fixation mechanism 1350 may have a functionality of fixing depressor 1345 to lever 1330.

FIGS. 17A, 17B, 18A, 18B, 19A, and 19B are schematic diagrams illustrating a single-component scleral depressor. FIG. 17A illustrates a side view of single-component scleral depressor with an actuated lever 1700. FIG. 17B illustrates a cross-sectional view in a sagittal plane of a single-component scleral depressor with an actuated lever 1700. FIG. 18A illustrates a superior view of a single-component scleral depressor with an actuated lever 1800. FIG. 18B illustrates a cross-sectional view in a frontal plane of a single-component scleral depressor with an actuated lever 1801. FIG. 19A illustrates a side view of a single-component scleral depressor with an unactuated lever 1900. FIG. 19B illustrates a cross-sectional view in a sagittal plane of a single-component scleral depressor with an unactuated lever 1900.

In one or more embodiments, a single-component scleral depressor may comprise an integral container 1705, an integral actuation platform 1715, an integral compression spring 1720, an integral pin 1725, an integral lever 1730, an integral lever control 1740, and an integral depressor 1745. Illustratively, integral container 1705 may comprise an integral container superior end 1706 and an integral container inferior end 1707. In one or more embodiments, integral container 1705 may comprise an integral actuation platform housing 1708. Illustratively, integral container 1705 may comprise an integral lever guide 1718. In one or more embodiments, integral container 1705 may comprise an integral inferior concavity 1755. Illustratively, integral container 1705 may comprise an integral superior concavity 1756. In one or more embodiments, integral container 1705 may comprise an integral compression spring superior interface 1709. Illustratively, integral actuation platform 1715 may comprise an integral compression spring inferior interface 1717. In one or more embodiments, integral actuation platform 1715 may comprise an integral pin guide 1716. Illustratively, integral actuation platform 1715 may be disposed in integral container 1705, e.g., integral actuation platform 1715 may be disposed in integral actuation platform housing 1708. In one or more embodiments, integral pin 1725 may be disposed in integral pin housing 1716. Illustratively, integral actuation platform 1715 may be configured to actuate about integral pin 1725, e.g., integral actuation platform 1715 may be configured to rotate about integral pin 1725 in a first direction and in a second direction.

In one or more embodiments, integral compression spring 1720 may be disposed in integral container 1705, e.g., integral compression spring 1720 may be disposed in integral actuation platform housing 1708. Illustratively, integral compression spring 1720 may be disposed between integral actuation platform 1715 and integral compression spring superior interface 1709. In one or more embodiments, a first end of integral compression spring 1720 may be adjacent to integral compression spring superior interface 1709 and a second end of integral compression spring 1720 may be adjacent to integral compression spring superior interface 1717, e.g., a first end of integral compression spring 1720 may abut integral compression spring superior interface 1709 and a second end of integral compression spring 1720 may abut integral compression spring superior interface 1717. Illustratively, integral compression spring 1720 may be configured to apply a force to a portion of integral actuation platform 1715, e.g., integral compression spring 1720 may be configured to apply a force to a portion of integral actuation platform 1715 configured to resist a rotation of integral actuation platform 1715 about integral pin 1725 in a first direction. In one or more embodiments, integral compression spring 1720 may be configured to apply a force to a portion of integral actuation platform 1715 configured to facilitate a rotation of integral actuation platform 1715 about integral pin 1725 in a second direction. Illustratively, integral lever 1730 may comprise an integral lever control 1740, e.g., integral lever control 1740 may comprise an integral lever control superior end 1742. In one or more embodiments, integral lever 1730 may comprise an integral depressor 1745. For example, integral lever 1730 may comprise an integral lever outer diameter 1760. Illustratively, a portion of integral lever 1730 may be disposed in integral container 1705, e.g., a portion of integral lever 1730 may be disposed in integral lever guide 1718. In one or more embodiments, integral lever 1730 may be configured to actuate within integral lever guide 1718.

In one or more embodiments, a user may apply a force to integral lever control 1740 of a single-component scleral depressor with an unactuated lever 1900, e.g., a user may apply a force to a portion of integral lever 1730 of a single-component scleral depressor with an unactuated lever 1900. Illustratively, an application of a force to integral lever 1730 of a single-component scleral depressor with an unactuated lever 1900 may be configured to actuate integral lever 1730 within integral lever guide 1718. In one or more embodiments, an actuation of integral lever 1730 within integral lever guide 1718 may be configured to rotate integral actuation platform 1715 about integral pin 1725, e.g., an actuation of integral lever 1730 within integral lever guide 1718 may be configured to rotate integral actuation platform 1715 about integral pin 1725 in a first direction. Illustratively, integral compression spring 1720 may be configured to apply a force to a portion of integral actuation platform 1715 configured to resist a rotation of integral actuation platform 1715 about integral pin 1725 in a first direction. In one or more embodiments, an actuation of integral actuation platform 1715 in a first direction may be configured to depress a patient's sclera, e.g., integral depressor 1745 may be configured to apply a force to a patient's sclera causing the patient's sclera to deform. Illustratively, a single-component scleral depressor may comprise a single-component scleral depressor with an actuated lever 1700 when a patient's sclera is depressed.

In one or more embodiments, a user may reduce or remove a force applied to integral lever control 1740 of a single-component scleral depressor with an actuated lever 1700, e.g., a user may reduce or remove a force applied to a portion of integral lever 1730 of a single-component scleral depressor with an actuated lever 1700. Illustratively, a reduction or a removal of a force applied to integral lever 1730 of a single-component scleral depressor with an actuated lever 1700 may be configured to actuate integral lever 1730 within integral lever guide 1718. In one or more embodiments, an actuation of integral lever 1730 within integral lever guide 1718 may be configured to rotate integral actuation platform 1715 about integral pin 1725, e.g., an actuation of integral lever 1730 within integral lever guide 1718 may be configured to rotate integral actuation platform 1715 about integral pin 1725 in a second direction. Illustratively, integral compression spring 1720 may be configured to apply a force to a portion of integral actuation platform 1715 configured to facilitate a rotation of integral actuation platform 1715 about integral pin 1725 in a second direction. In one or more embodiments, an actuation of integral actuation platform 1715 in a second direction may be configured to raise a patient's sclera, e.g., integral depressor 1745 may be configured to reduce or remove a force applied to a patient's sclera causing the patient's sclera to deform. Illustratively, a single-component scleral depressor may comprise a single-component scleral depressor with an unactuated lever 1900 when a patient's sclera is raised.

Illustratively, one or more portions of a single-component scleral depressor may be manufactured by additive manufacturing, e.g., one or more portions of a single-component scleral depressor may be manufactured by selective laser sintering, selective heat sintering, selective laser melting, electron-beam melting, direct metal laser sintering, electron beam freeform fabrication, stereolithography, digital light processing, fused deposition modeling, laminated object manufacturing, ultrasonic additive manufacturing, vat photopolymerization, material jetting, binder jetting, laser engineered net shaping, etc. In one or more embodiments, a single-component scleral depressor may be manufactured entirely by additive manufacturing, e.g., a single-component scleral depressor may be manufactured entirely by selective laser sintering, selective heat sintering, selective laser melting, electron-beam melting, direct metal laser sintering, electron beam freeform fabrication, stereolithography, digital light processing, fused deposition modeling, laminated object manufacturing, ultrasonic additive manufacturing, vat photopolymerization, material jetting, binder jetting, laser engineered net shaping, etc. For example, a single-component scleral depressor may be manufactured by selective laser sintering from a nylon material.

Illustratively, integral container 1705 may be manufactured by additive manufacturing wherein one or more subcomponents of a multi-component scleral depressor assembly 1300 are eliminated but a functionality of the one or more subcomponents is retained, e.g., integral container 1705 eliminates upper container 1305 and lower container 1310 as subcomponents but retains a functionality of housing integral actuation platform 1715 and integral compression spring 1720. In one or more embodiments, integral compression spring 1720 may be manufactured by additive manufacturing wherein one or more subcomponents of a multi-component scleral depressor assembly 1300 are eliminated but a functionality of the one or more subcomponents is retained, e.g., integral compression spring 1720 eliminates compression spring 1320 as a subcomponent but retains of functionality of applying a force to a portion of integral actuation platform 1715. Illustratively, integral actuation platform 1715 may be manufactured by additive manufacturing wherein one or more subcomponents of a multi-component scleral depressor assembly 1300 are eliminated but a functionality of the one or more subcomponents is retained, e.g., integral actuation platform 1715 eliminates actuation platform 1315 as a subcomponent but retains a functionality of counterbalancing integral lever 1730. In one or more embodiments, integral lever control 1740 may be manufactured by additive manufacturing wherein one or more subcomponents of a multi-component scleral depressor assembly 1300 are eliminated but a functionality of the one or more subcomponents is retained, e.g., integral lever control 1740 eliminates lever control 1340 as a subcomponent but retains a functionality of facilitating an actuation of integral lever 1730. Illustratively, integral depressor 1745 may be manufactured by additive manufacturing wherein one or more subcomponents of a multi-component scleral depressor assembly 1300 are eliminated but a functionality of the one or more subcomponents is retained, e.g., integral depressor 1745 eliminates depressor 1345 and depressor fixation mechanism 1350 as subcomponents but retains a functionality of fixing integral depressor 1745 to integral lever 1730.

Illustratively, an economic feasibility of subcomponent integration by additive manufacturing may be unique to surgical instruments, e.g., an economic feasibility of subcomponent integration by additive manufacturing may be unique to ophthalmic surgical instruments. For example, unlike consumer goods, e.g., automobiles, watches, telephones, etc., a market size for ophthalmic surgical instruments is limited by a medical need to perform a particular ophthalmic surgical procedure requiring a particular ophthalmic surgical instrument. Illustratively, a technological feasibility of subcomponent integration by additive manufacturing may be unique to surgical instruments, e.g., a technological feasibility of subcomponent integration by additive manufacturing may be unique to ophthalmic surgical instruments. For example, dimensional tolerances of additive manufacturing processes may be unique to ophthalmic surgical instruments.

In one or more embodiments, surgical instrument subcomponent integration by additive manufacturing may comprise identifying a surgical instrument component having at least three subcomponents wherein each subcomponent of the at least three subcomponents has at least one functionality, e.g., a first subcomponent may have a first functionality, a second subcomponent may have a second functionality, and a third subcomponent may have a third functionality. Illustratively, surgical instrument subcomponent integration by additive manufacturing may comprise identifying a surgical instrument component having at least three subcomponents wherein each subcomponent of the at least three subcomponents has at least one functionality and wherein each subcomponent of the at least three subcomponents may be mechanically separated from the surgical instrument component assembly without losing the at least one functionality, e.g., a first subcomponent may have a first functionality, a second subcomponent may have a second functionality, and a third subcomponent may have a third functionality wherein the first functionality is independent of the second functionality and the third functionality and wherein the second functionality is independent of the first functionality and the third functionality and wherein the third functionality is independent of the first functionality and the second functionality. Illustratively, surgical instrument subcomponent integration by additive manufacturing may comprise identifying a surgical instrument component having at least three subcomponents wherein each subcomponent of the at least three subcomponents is manufactured from a unique material, e.g., a first subcomponent may be manufactured from a first material, a second subcomponent may be manufactured from a second material, and a third subcomponent may be manufactured from a third material. In one or more embodiments, surgical instrument subcomponent integration by additive manufacturing may comprise identifying a surgical instrument component having at least three subcomponents wherein each subcomponent of the at least three subcomponents is manufactured from a material that is different from a material used in an additive manufacturing process to integrate the at least three subcomponents, e.g., a first subcomponent may be manufactured from a first material, a second subcomponent may be manufactured from a second material, a third subcomponent may be manufactured from a third material, and a fourth material may be used in an additive manufacturing process to integrate the first subcomponent, the second subcomponent, and the third subcomponent.

In one or more embodiments, surgical instrument subcomponent integration by additive manufacturing may comprise identifying a surgical instrument component having at least two subcomponents wherein each subcomponent of the at least two subcomponents has at least one functionality, e.g., a first subcomponent may have a first functionality and a second subcomponent may have a second functionality. Illustratively, surgical instrument subcomponent integration by additive manufacturing may comprise identifying a surgical instrument component having at least two subcomponents wherein each subcomponent of the at least two subcomponents has at least one functionality and wherein each subcomponent of the at least two subcomponents may be mechanically separated from the surgical instrument component assembly without losing the at least one functionality, e.g., a first subcomponent may have a first functionality and a second subs component may have a second functionality wherein the first functionality is independent of the second functionality and wherein the second functionality is independent of the first functionality. Illustratively, surgical instrument subcomponent integration by additive manufacturing may comprise identifying a surgical instrument component having at least two subcomponents wherein each subcomponent of the at least two subcomponents is manufactured from a unique material, e.g., a first subcomponent may be manufactured from a first material and a second subcomponent may be manufactured from a second material. In one or more embodiments, surgical instrument subcomponent integration by additive manufacturing may comprise identifying a surgical instrument component having at least two subcomponents wherein each subcomponent of the at least two subcomponents is manufactured from a material that is different from a material used in an additive manufacturing process to integrate the at least two subcomponents, e.g., a first subcomponent may be manufactured from a first material and a second subcomponent may be manufactured from a second material, and a third material may be used in an additive manufacturing process to integrate the first subcomponent and the second subcomponent.

Illustratively, surgical instrument subcomponent integration by additive manufacturing may comprise modifying one or more properties of a subcomponent of a multi-component assembly for integration, e.g., spring 150 may be manufactured from a first material having a first Young's modulus and integral spring 350 may be manufactured by additive manufacturing from a second material having a second Young's modulus. In one or more embodiments, surgical instrument subcomponent integration by additive manufacturing may comprise modifying a dimension of a subcomponent of a multi-component assembly for integration, e.g., spring 150 may have a first length and a spring constant and integral spring 350 may have a second length configured to reproduce the spring constant. Illustratively, the first length may be greater than the second length. In one or more embodiments, the second length may be greater than the first length. Illustratively, spring 150 may have a first cross-sectional area and a spring constant and integral spring 350 may have a second cross-sectional area configured to reproduce the spring constant. In one or more embodiments, the first cross-sectional area may be greater than the second cross-sectional area. Illustratively, the second cross-sectional area may be greater than the first cross-sectional area.

In one or more embodiments, surgical instrument subcomponent integration by additive manufacturing may compromise modifying one or more properties of a subcomponent of a multi-component assembly for integration and fixation, e.g., a portion of hypodermic tube 110 may be fixed in hypodermic tube housing 126 by a first interference fit and one or more properties of integral hypodermic tube housing 363 may be modified to reproduce the first interference fit. Illustratively, nosecone 120 may be manufactured from a first material and single-component tip base 320 may be manufactured from a second material, e.g., hypodermic tube 110 and hypodermic tube housing 126 may have a first coefficient of friction and hypodermic tube 110 and integral hypodermic tube housing 363 may have a second coefficient of friction. In one or more embodiments, the first coefficient of friction between hypodermic tube 110 and hypodermic tube housing 126 may be less than the second coefficient of friction between hypodermic tube 110 and integral hypodermic tube housing 363. Illustratively, the first coefficient of friction between hypodermic tube 110 and hypodermic tube housing 126 may be greater than the second coefficient of friction between hypodermic tube 110 and integral hypodermic tube housing 363. In one or more embodiments, nosecone 120 may be manufactured from a first material having a first density and single-component tip base 320 may be manufactured from a second material having a second density. Illustratively, the first density of the first material may be greater than the second density second material. In one or more embodiments, the first density of the first material may be less than the second density second material. Illustratively, nosecone 120 may be manufactured from a first material having a first modulus of elasticity and single-component tip base 320 may be manufactured from a second material having a second modulus of elasticity. In one or more embodiments, the first modulus of elasticity of the first material may be greater than the second modulus of elasticity of the second material. Illustratively, the first modulus of elasticity of the first material may be less than the second modulus of elasticity of the second material. In one or more embodiments, surgical instrument subcomponent integration by additive manufacturing may compromise modifying an inner diameter of a subcomponent of a multi-component assembly for integration and fixation, e.g., nosecone 120 may be manufactured from a first material having a first set of material properties and hypodermic tube housing 126 may have an inner diameter of a first size wherein hypodermic tube 110 may be fixed in hypodermic tube housing 126 by a first interference fit and single-component tip base 320 may be manufactured by additive manufacturing from a second material having a second set of material properties and integral hypodermic tube housing 363 may have an inner diameter of a second size wherein the inner diameter of the second size is configured to reproduce the first interference fit when hypodermic tube 110 is inserted into integral hypodermic tube housing 363. Illustratively, the inner diameter of the first size may be greater than the inner diameter of the second size. In one or more embodiments, the inner diameter of the first size may be less than the inner diameter of the second size.

In one or more embodiments, a portion of housing tube sleeve 610 may be fixed in piston tube inner lumen 675 by a first interference fit and one or more properties of integral piston tube inner lumen 975 may be modified to reproduce the first interference fit. Illustratively, piston tube 630 may be manufactured from a first material and integral piston tube 930 may be manufactured from a second material, e.g., housing tube sleeve 610 and piston tube inner lumen 975 may have a first coefficient of friction and housing tube sleeve 610 and integral piston tube inner lumen 975 may have a second coefficient of friction. In one or more embodiments, the first coefficient of friction between housing tube sleeve 610 and piston tube inner lumen 975 may be less than the second coefficient of friction between housing tube sleeve 610 and integral piston tube inner lumen 975. Illustratively, the first coefficient of friction between housing tube sleeve 610 and piston tube inner lumen 975 may be greater than the second coefficient of friction between housing tube sleeve 610 and integral piston tube inner lumen 975. In one or more embodiments, piston tube 630 may be manufactured from a first material having a first density and integral piston tube 930 may be manufactured from a second material having a second density. Illustratively, the first density of the first material may be greater than the second density second material. In one or more embodiments, the first density of the first material may be less than the second density second material. Illustratively, piston tube 630 may be manufactured from a first material having a first modulus of elasticity and integral piston tube 930 may be manufactured from a second material having a second modulus of elasticity. In one or more embodiments, the first modulus of elasticity of the first material may be greater than the second modulus of elasticity of the second material. Illustratively, the first modulus of elasticity of the first material may be less than the second modulus of elasticity of the second material. In one or more embodiments, surgical instrument subcomponent integration by additive manufacturing may compromise modifying an inner diameter of a subcomponent of a multi-component assembly for integration and fixation, e.g., piston tube 630 may be manufactured from a first material having a first set of material properties and piston tube inner lumen 675 may have an inner diameter of a first size wherein housing tube sleeve 610 may be fixed in piston tube inner lumen 675 by a first interference fit and integral piston tube 930 may be manufactured by additive manufacturing from a second material having a second set of material properties and integral piston tube inner lumen 975 may have an inner diameter of a second size wherein the inner diameter of the second size is configured to reproduce the first interference fit when housing tube sleeve 610 is inserted into integral piston tube inner lumen 975. Illustratively, the inner diameter of the first size may be greater than the inner diameter of the second size. In one or more embodiments, the inner diameter of the first size may be less than the inner diameter of the second size.

Illustratively, surgical instrument subcomponent integration by additive manufacturing may compromise modifying one or more properties of a subcomponent of a multi-component assembly for integration and operation, e.g., lever 1330 may have a first stiffness and one or more properties of integral lever 1730 may be modified to reproduce the first stiffness. In one or more embodiments, lever 1330 may be manufactured from a first material having a first density and integral lever 1730 may be manufactured from a second material having a second density. Illustratively, the first density of the first material may be greater than the second density second material. In one or more embodiments, the first density of the first material may be less than the second density second material. Illustratively, lever 1330 may be manufactured from a first material having a first modulus of elasticity and integral lever 1730 may be manufactured from a second material having a second modulus of elasticity. In one or more embodiments, the first modulus of elasticity of the first material may be greater than the second modulus of elasticity of the second material. Illustratively, the first modulus of elasticity of the first material may be less than the second modulus of elasticity of the second material. In one or more embodiments, surgical instrument subcomponent integration by additive manufacturing may compromise modifying an outer diameter of a subcomponent of a multi-component assembly for integration and operation, e.g., lever 1330 may be manufactured from a first material having a first set of material properties and lever outer diameter 1360 may be a first size wherein lever 1330 has a first stiffness and integral lever 1730 may be manufactured by additive manufacturing from a second material having a second set of material properties and integral lever outer diameter 1760 may be a second size wherein the second size is configured to reproduce the first stiffness. Illustratively, the first size may be greater than the second size. In one or more embodiments, the first size may be less than the second size.

In one or more embodiments, surgical instrument subcomponent integration by additive manufacturing may comprise modifying a design of a subcomponent of a multi-component assembly for integration, e.g., superior fixation mechanism 140 and inferior fixation mechanism 143 may have a first mechanism of function and a functionality and integral fixation mechanism 340 may have a second mechanism of function configured to reproduce the functionality. Illustratively, laser probe distal fixation mechanism 620, control mechanism 625, and piston tube 630 may have a first mechanism of function and a functionality and control mechanism anchor 901, control mechanism anchor guide 905, integral control mechanism 925 and integral piston tube 930 may have a second mechanism of function configured to reproduce the functionality.

In one or more embodiments, an assembled multi-component surgical instrument may have a first cost associated with subcomponents, a first cost associated with manufacturing, and a first total cost wherein the first total cost is the sum of the first cost associated with subcomponents and the first cost associated with manufacturing. Illustratively, an assembled single-component surgical instrument may have a second cost associated with subcomponents, a second cost associated with manufacturing, and a second total cost wherein the second total cost is the sum of the second cost associated with subcomponents and the second cost associated with manufacturing. In one or more embodiments, the second cost associated with subcomponents may include a cost of subcomponent integration by additive manufacturing and the second cost associated with manufacture may not include a cost of subcomponent integration by additive manufacturing. Illustratively, the first cost associated with subcomponents may be less than the second cost associated with subcomponents. In one or more embodiments, the first cost associated with subcomponents may be greater than the second cost associated with subcomponents. Illustratively, the first cost associated with subcomponents may be equal to the second cost associated with subcomponents. In one or more embodiments, the first cost associated with manufacturing may be less than the second cost associated with manufacturing. Illustratively, the first cost associated with manufacturing may be greater than the second cost associated with manufacturing. In one or more embodiments, the first cost associated with manufacturing may be equal to the second cost associated with manufacturing. Illustratively, the first total cost may be less than the second total cost. In one or more embodiments, the first total cost may be greater than the second total cost. Illustratively, the first total cost may be equal to the second total cost.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of surgical instrument subcomponent integration, the teachings of the present invention are equally suitable to any systems where the functionality may be employed. Therefore, it is the object of the appended claims to cover all such variations and modifications as come within the true spirit and scope of the invention.

What is claimed is:

1. An integrated surgical instrument component manufactured by additive manufacturing of a single-component surgical instrument comprising:
   an integral spring of the integrated surgical instrument component wherein the integral spring is manufactured from a first material having a first Young's modulus and has an integral spring length and an integral spring cross-sectional area;
   a single-component tip base having a single-component tip base distal end and a single component tip base proximal end wherein the single-component tip base is manufactured from the first material and wherein the integral spring is disposed in the single-component tip base and wherein the single-component tip base;
   a hypodermic tube having a hypodermic tube distal end, a hypodermic tube proximal end, and a hypodermic tube inner lumen wherein the hypodermic tube proximal end is disposed in an integral hypodermic tube housing of the single-component tip base and wherein a portion of the hypodermic tube is fixed in the integral hypodermic tube housing by an interference fit;
   an integral fixation mechanism disposed in the single-component tip base wherein the integral fixation mechanism is manufactured from the first material;
   an integral proximal fixation mechanism of the single-component tip base wherein the integral proximal fixation mechanism is manufactured from the first material; and
   an integral extension mechanism of the single-component tip base wherein the integral extension mechanism is manufactured from the first material.

2. The integrated surgical instrument component of claim 1 further comprising:
   a snap-fit release member of the integral fixation mechanism wherein the snap fit release member is manufactured from the first material.

3. The integrated surgical instrument component of claim 1 further comprising:
   a snap-fit release guide of the integral fixation mechanism wherein the snap fit release guide is manufactured from the first material.

4. The integrated surgical instrument component of claim 1 further comprising:
   a first snap-fit limb of the integral fixation mechanism wherein the first snap-fit limb is manufactured from the first material.

5. The integrated surgical instrument component of claim 4 further comprising:
   a first snap-fit limb lock of the first snap-fit limb wherein the first snap-fit limb lock is manufactured from the first material.

6. The integrated surgical instrument component of claim 5 further comprising:
   a second snap-fit limb of the integral fixation mechanism wherein the second snap fit limb is manufactured from the first material.

7. The integrated surgical instrument component of claim 6 further comprising:
   a second snap-fit limb lock of the second snap-fit limb wherein the second snap-fit limb lock is manufactured from the first material.

8. The integrated surgical instrument component of claim 1 further comprising:
   a tip protector interface of the single-component tip base wherein the tip protector interface is manufactured from the first material.

9. The integrated surgical instrument component of claim 1 further comprising:
   an integral identification ring of the single-component tip base wherein the integral identification ring is manufactured from the first material.

10. The integrated surgical instrument component of claim 1 further comprising:
    a flange of the single-component tip base wherein the flange is manufactured from the first material.

11. The integrated surgical instrument component of claim 1 further comprising:
    a blank having a blank distal end and a blank proximal end wherein the blank is disposed in the hypodermic tube and the single-component tip base.

12. The integrated surgical instrument component of claim 11 wherein the integral fixation mechanism is configured to fix the blank in a position relative to the hypodermic tube.

13. The integrated surgical instrument component of claim 12 further comprising: instrument jaws of the blank.

14. The integrated surgical instrument component of claim 13 wherein an extension of the hypodermic tube relative to the blank is configured to close the instrument jaws.

15. The integrated surgical instrument component of claim 13 wherein an extension of the hypodermic tube relative to the blank is configured to close the instrument jaws.

* * * * *